United States Patent [19]

Lok et al.

[11] Patent Number: 4,683,217
[45] Date of Patent: Jul. 28, 1987

[54] IRON-ALUMINUM-PHOSPHORUS-SILICON-OXIDE MOLECULAR SIEVES

[75] Inventors: Brent M. Lok, New City; Lawrence D. Vail, New Rochelle; Edith M. Flanigen, White Plains, all of N.Y.

[73] Assignee: Union Carbide Corporation, Danbury, Conn.

[21] Appl. No.: 600,173

[22] Filed: Apr. 13, 1984

[51] Int. Cl.⁴ .......................................... B01J 27/182
[52] U.S. Cl. .................................. 502/214; 423/306
[58] Field of Search ............. 423/306, 326, 328, 329; 502/60, 62, 77, 162, 164, 214, 213

[56] References Cited

U.S. PATENT DOCUMENTS

| | | | |
|---|---|---|---|
| 4,208,305 | 6/1980 | Kouwenhoven et al. | 423/326 X |
| 4,310,440 | 1/1982 | Wilson et al. | 423/305 |
| 4,420,467 | 12/1983 | Whittam | 423/328 |
| 4,440,871 | 4/1984 | Lok et al. | 502/214 |
| 4,456,582 | 6/1984 | Marosi et al. | 423/326 X |
| 4,486,397 | 12/1984 | Eshraghi et al. | 502/208 X |
| 4,500,651 | 2/1985 | Lok et al. | 502/208 |
| 4,554,143 | 11/1985 | Messina et al. | 423/306 |

FOREIGN PATENT DOCUMENTS

| | | |
|---|---|---|
| 0054364 | 6/1982 | European Pat. Off. . |
| 0055046 | 6/1982 | European Pat. Off. . |
| 0055529 | 7/1982 | European Pat. Off. . |
| 0059059 | 9/1982 | European Pat. Off. . |
| 0147991 | 7/1985 | European Pat. Off. ............ 502/214 |

OTHER PUBLICATIONS

Haggin, C & En, Jun. 20, 1983, pp. 36–37.

Primary Examiner—William R. Dixon, Jr.
Assistant Examiner—R. Bruce Breneman
Attorney, Agent, or Firm—Vincent J. Vasta, Jr.

[57] ABSTRACT

A novel class of iron-aluminum-phosphorus-silicon-oxide molecular sieves is disclosed which contain as framework constituents $FeO_2^-$, and/or $FeO_2^{-2}$, $AlO_2^-$, $PO_2^+$, and $SiO_2$ tetrahedral oxide units. These compositions are prepared hydrothermally, perferably using organic templating agents and are suitably employed as adsorbents and catalysts.

26 Claims, 3 Drawing Figures

IRON-ALUMINUM-PHOSPHORUS-SILICON-OXIDE MOLECULAR SIEVES

FIELD OF THE INVENTION

The instant invention relates to a novel class of crystalline microporous iron-aluminum-phosphorus-silicon-oxide molecular sieves, and to the method for their preparation. These molecular sieve compositions are prepared hydrothermally from gels containing reactive compounds of iron, phosphorus, silicon and aluminum and preferably at least one organic templating agent (or "template") which functions in part to determine the course of the crystallization mechanism and hence the structure of the molecular sieve products.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982, there is described a novel class of silicon-substituted aluminophosphates which are both microporous and crystalline. The materials have a three-dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

$$mR: (Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned application Ser. No. 480,738, filed Mar. 31, 1983 there is described a novel class of titanium-containing molecular sieves whose chemical composition in the as-synthesized and anhydrous form is represented by the unit empirical formula:

$$mR: (Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In copending and commonly assigned application Ser. No. 514,334, filed July 15, 1983, there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y" and "z" represent the mole fraction of the metal "M", aluminum and phosphorus, respectively, present as tetrahedral oxides.

In copending and commonly assigned application Ser. No. 514,335, filed July 15, 1983, there is described a novel class of crystalline ferroaluminophosphates having a three-dimensional microporous framework structure of $FeO_2$, $AlO_2$ and $PO_2$ tetrahedral units and having an empirical chemical composition on an anhydrous basis expressed by the formula $$mR: (Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fraction of the iron, aluminum and phosphorus, respectively, present as tetrahedral oxides.

The instant invention relates to new iron-aluminum-phosphorus-silicon-oxide molecular sieves having three-dimensional microporous crystal framework structures of $FeO_2^{2-}$ (or $FeO_2^{-1}$), $AlO_2^{-}$, $PO_2^{+}$ and $SiO_2$ tetrahedral units.

SUMMARY OF THE INVENTION

A novel class of iron-aluminum-phosphorus-silicon-oxide molecular sieves having use as adsorbents, ion-exchange media, catalysts, etc. are disclosed having three-dimensional microporous crystal framework structures of $FeO_2^{-2}$ (for convenience herein any reference to $FeO_2^{-2}$ is meant to also denote reference to $FeO_2^{-1}$), $AlO_2^{-}$, $PO_2^{+}$ and $SiO_2$ tetrahedral units and having a unit empirical formula, on an anhydrous basis, of:

wherein "R" represents at least one organic templating agent present in the intracrystalline pore system; "m" represents the moles of "R" present per mole of $(Fe_wAl_xP_ySi_z)_2$ and has a value of from zero (0) to about 0.3; and "x", "x", "y" and "z" represent the mole fractions of iron, aluminum, phosphorus and silicon, respectively, present as tetrahedral oxides. The molecular sieves of the present invention are generally employable as catalysts for various hydrocarbon conversion processes, molecular separations and miscellaneous processes. The instant molecular sieve compositions are characterized in several ways as distinct from heretofore known molecular sieves, including the aforementioned ternary compositions. The instant molecular sieves are characterized by the enhanced thermal stability of certain species and by the existence of species heretofore unknown for binary and ternary molecular sieves.

Since the designation of the molecular sieves as "iron-aluminum-phosphorus-silicon-oxide molecular sieves" is somewhat cumbersome, the "iron-aluminum-phosphorus-silicon-oxide sieves" of this invention will be referred to hereinafter by the shorthand reference "FeAPSO" to identify the various structural species which make up the FeAPSO class. Each species is assigned a number, e.g., "FeAPSO-i", and is identified, for example, as FeAPSO-5, FeAPSO-11 and so forth where "i" is an integer specific to a given class member as its preparation is reported herein. This designation is an arbitrary one and is not intended to denote structural relationship to another material(s) which may also be characterized by a numbering system.

DETAILED DESCRIPTION OF THE INVENTION

Figure 1:
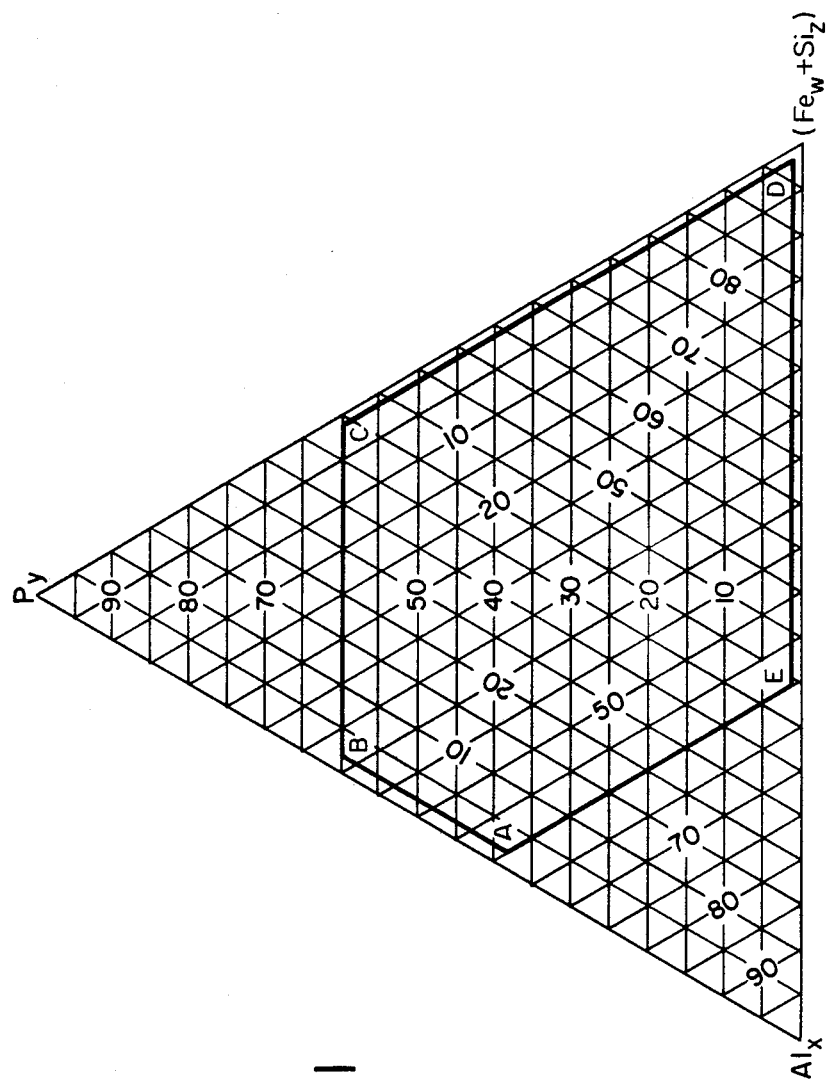
FIG. 1 is a ternary diagram wherein parameters relating to the instant compositions are set forth as mole fractions.

The instant invention relates to a novel class of iron-aluminum-phosphorus-silicon-oxide molecular sieves having a three-dimensional microporous crystal framework structures of $FeO_2^{-2}$ (and/or $FeO_2^{-}$), $AlO_2^{-}$, $PO_2^{+}$ and $SiO_2$ tetrahedral oxide units and having a unit empirical formula, on an anhydrous basis, of:

$$mR: (Fe_wAl_xP_ySi_z)O_2 \quad (1)$$

wherein "R" represents at least one organic templating agent present in the intracrystalline pore system; "m" represents the moles of "R" present per mole of $(Fe_wAl_xP_ySi_z)O_2$ and has a value of from zero (0) to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the pentagonal compositional area defined by points A, B, C, D and E of the ternary diagram which is FIG. 1 of the drawings and more preferably are within the tetragonal compositional area defined by points a, b, c, and d of the ternary diagram which is FIG. 2 of the drawings. Points A, B, C, D and E of FIG. 1 represent the following values for "w", "x", "y" and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

Figure 2:
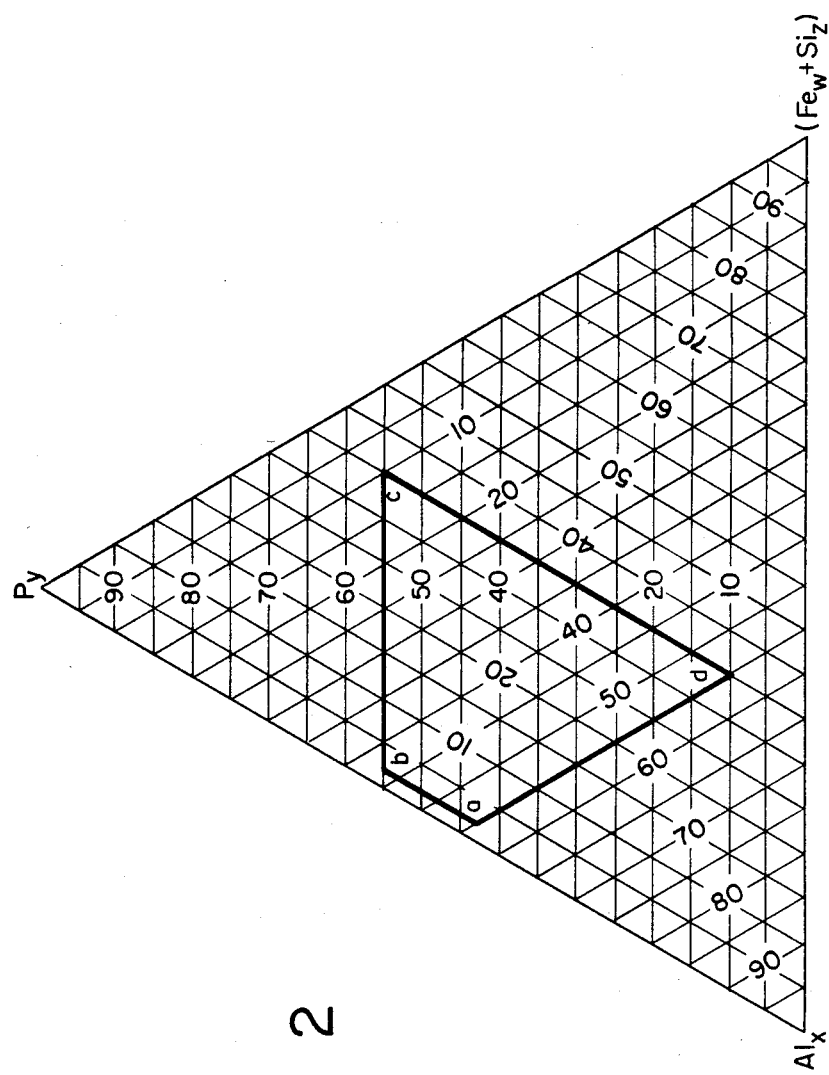
FIG. 2 is a ternary diagram wherein parameters relating to preferred compositions are set forth as mole fractions.

Points a, b, c and d of FIG. 2 represent the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The term "unit empirical formula" is used herein according to its common meaning to designate the simplest formula which gives the relative number of moles of iron, aluminum, phosphorus, and silicon which form the $FeO_2^{-2}$, $AlO_2^{-}$, $PO_2^{+}$ and $SiO_2$ tetrahedral units of the FeAPSO and which form the molecular framework of the FeAPSO composition(s). The unit empirical formula is given in terms of iron, aluminum, phosphorus and silicon and does not include other compounds, cations or anions which may be present as a result of the preparation or existence of other impurities or materials in the bulk composition not containing the aforementioned tetrahedral unit. The amount of template R is reported as part of the composition when the as-synthesized unit empirical formula is given, and water may also be reported unless such is defined as the anhydrous form.

The unit empirical formula for a FeAPSO may be given on an "as-synthesized" basis or may be given after an "as-synthesized" FeAPSO composition has been subjected to some post treatment process, e.g., calcination. The term "as-synthesized" herein shall be used to refer to the FeAPSO composition(s) formed as a result of the hydrothermal crystallization but before the FeAPSO composition has been subjected to post treatment to remove any volatile components present therein. The actual value of "m" for a post-treated FeAPSO will depend on several factors (including: the particular FeAPSO, template, severity of the post-treatment in terms of its ability to remove the template from the FeAPSO, the proposed application of the FeAPSO composition, and etc.) and the value for "m" can be within the range of values as defined for the as-synthesized FeAPSO compositions, although such is generally less than the as-synthesized FeAPSO unless such post-treatment process adds template to the FeAPSO so treated. A FeAPSO composition which is in the calcined or other post-treatment form generally has an empirical formula represented by formula (1), except that the value of "m" is a calcined FeAPSO is generally less than about 0.02. Under sufficiently severe post-treatment conditions, e.g. roasting in air at high temperature for long periods (over 1 hr.), the value of "m" may be zero (0) or, in any event, the template, R, is undetectable by normal analytical procedures.

The FeAPSOs of this new class of compositions will exhibit molecular sieving properties similar to zeolitic aluminosilicates and are capable of reversibly absorbing water and other molecular species. While it is believed that iron, aluminum, phosphorus and silicon framework constituents are present in tetrahedral coordination with oxygen, i.e. as tetrahedral oxide units, it is theoretically possible that some fraction, probably minor, of these framework constituents are present in coordination with five or six oxygen atoms. It is not, moreover, necessarily the case that all the iron, aluminum, phosphorus and/or silicon of any given synthesized product be part of the framework in the aforementioned types of coordination with oxygen. Some of each constituent may be in some as yet undetermined form and may not be structurally significant.

Since the present FeAPSO compositions are formed from $FeO_2$, $AlO_2$, $PO_2$ and $SiO_2$ tetrahedral units which, respectively, have a net charge of $-2$ (or $-1$), $-1$, $+1$, and zero (0), the matter of cation exchangeability is considerably more complicated than in the case of zeolitic molecular sieves in which, ideally, there is a stoichiometric relationship between $AlO_2^-$ tetrahedra and charge-balancing cations. In the FeAPSO compositions, an $AlO_2^-$ tetrahedron can be balanced electrically either by association with a $PO_2^+$ tetrahedron or a simple cation such as an alkali metal cation, a proton ($H^+$), a cation of, e.g. $Fe^{2+}$ or $Fe^{3+}$, a complex cation present in the reaction mixture, or an organic cation derived from the templating agent. Similarly an $FeO_2^-$ or $FeO_2^{-2}$ tetrahedron can be balanced electrically by association with $PO_2^+$ tetrahedra, a cation of iron, a proton ($H^+$), an alkali metal cation, organic cation(s) derived from the templating agent, or other divalent or polyvalent metal cations introduced from an extraneous source. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, DC (1971)]

The FeAPSOs of the instant invention are generally synthesized by hydrothermal crystallization from a reaction mixture comprising reactive sources of iron, aluminum, phosphorus and silicon, and preferably one or more organic templating agents. Optionally, alkali or other metal(s) may be present in the reaction mixture and may act as templating agents. The reaction mixture is generally placed in a pressure vessel, preferably lined with an inert plastic material, such as polytetrafluoroethylene, and heated, preferably under the autogeneous pressure, at an effective temperature which is generally between about 50° C., and about 250° C. and preferably between about 100° C. and about 200° C., until crystals of the FeAPSO product are obtained. An effective time for obtaining FeAPSO products is generally a period from several hours to several weeks. Generally the crystallization times are from about 2 hours to about 30 days and typically from about 4 hours to about 20 days being employed to obtain FeAPSO crystals. While not essential to the synthesis of the instant molecular sieves, it has been found that in general stirring or other moderate agitation of the reaction mixture and/or seeding the reaction mixture with seed crystals of either the FeAPSO to be produced, or a topologically similar aluminosilicate, aluminophosphate or molecular sieve composition, facilitates the crystallization procedure. The product is recovered by any convenient method, such as centrifugation or filtration.

After crystallization the FeAPSO may be isolated and washed with water and dried in air. As a result of the hydrothermal crystallization, the as-synthesized FeAPSO generally contains within its intracrystalline pore system at least one form of the template employed in its formation. Generally, the template is a molecular species, but it is possible, steric considerations permitting, that at least some of the template is present as a charge-balancing cation. Generally the template is too large to move freely through the intracrystalline pore system of the formed FeAPSO and may be removed by a post-treatment process, such as by calcining the particular FeAPSO at temperatures of between about 200° C. and to about 700° C. so as to thermally degrade the template or by employing some other post-treatment process for removal of at least part of the template from the FeAPSO. In some instances the pores of the FeAPSO are sufficiently large to permit transport of the template, and, accordingly, complete or partial removal thereof can be accomplished by conventional desorption procedures such as carried out in the case of zeolites.

Figure 3:
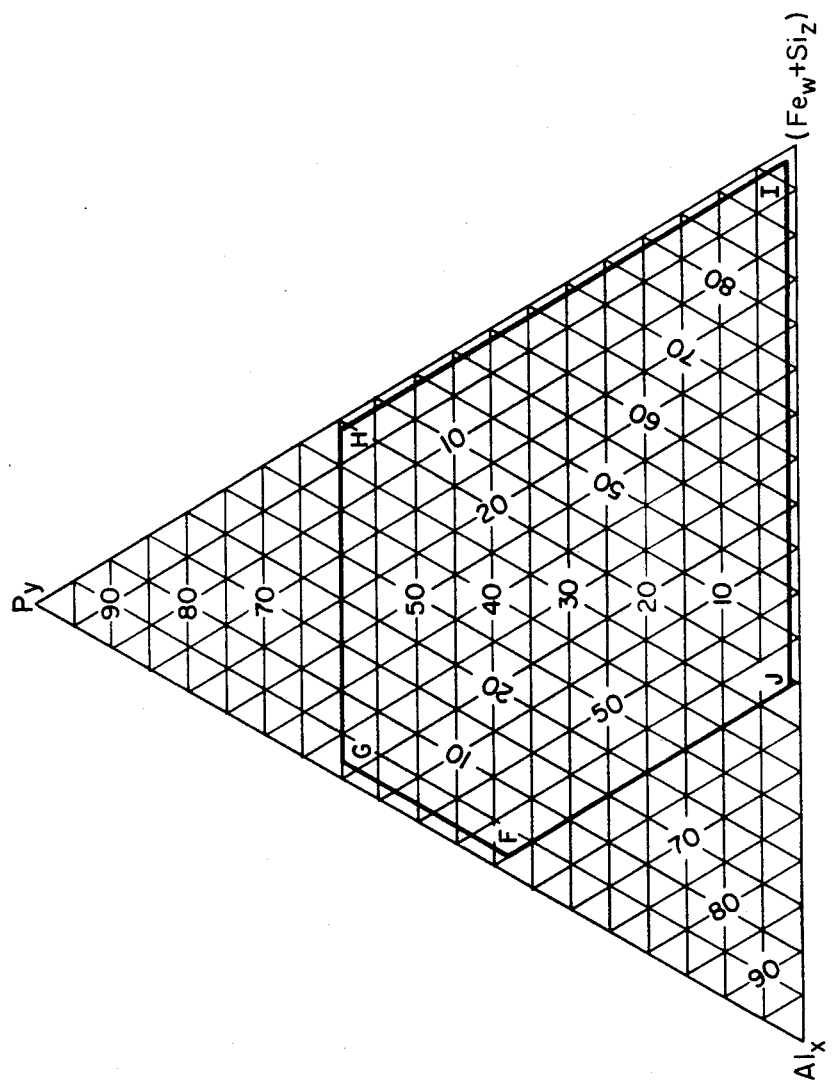
FIG. 3 is a ternary diagram wherein parameters relating to the reaction mixtures employed in the preparation of the compositions of this invention are set forth as mole fractions.

The FeAPSO compositions are generally formed from a reaction mixture containing reactive sources of iron, aluminum, phosphorus and silicon, and preferably an organic templating agent, said reaction mixture comprising a composition expressed in terms of molar oxide ratios of:

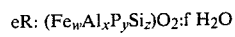

$$eR: (Fe_wAl_xP_ySi_z)O_2 : f\ H_2O$$

wherein "R" is an organic templating agent; "e" has a value of from zero to about 6 and is preferably an effective amount greater than zero to about 6; "f" has a value of from about zero to 500, preferably from about 2 to about 300; and "w", "x", "y" and "z" represent the mole fractions, respectively, of iron, aluminum, phosphorus and silicon in the $(Fe_wAl_xP_ySi_z)$ constituent, and each has a value of at least 0.01. In a preferred embodiment the reaction mixture is selected such that the mole fractions "w", "x", "y" and "z" are generally defined as being within the pentagonal compositional area defined by points F, G, H, I and J of the ternary diagram of FIG. 3. Points F, G, H, I and J of FIG. 3 have the following values for "w", "x", "y" and "z":

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

For reasons unknown at present, not every reaction mixture gives crystalline FeAPSO products when reaction products were examined for FeAPSO products by X-ray analysis. Those reaction mixtures from which crystalline FeAPSO products were obtained are reported in the examples hereinafter as numbered examples and those reaction mixtures from which FeAPSO products were not identified by use of X-ray analysis are reported as lettered examples.

In the foregoing expression of the reaction composition, the reactants are normalized with respect to the total of "w", "x", "y" and "z" such that $(w+x+y+z)=1.00$ mole, whereas in the examples the reaction mixtures are expressed in terms of molar oxide ratios which may be normalized to the moles of $P_2O_5$. This latter form is readily converted to the former form by routine calculations by dividing the number of moles of each component (including the template and water) by the total number of moles of iron, aluminum, phosphorus and silicon which results in normalized mole fractions based on total moles of the aforementioned components.

The reaction mixture from which the FeAPSOs are formed preferably contains one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen and are of the formula $R_4X^+$ wherein X is selected from the group consisting of nitrogen, phosphorus, arsenic and/or antimony and R may be hydrogen, alkyl, aryl, araalkyl, or alkylaryl group and is preferably aryl or alkyl containing between 1 and 8 carbon atoms, although more than eight carbon atoms may be present in each "R" group of the template. Templates which are preferred include amines, quaternary phosphonium compounds, and quaternary compounds ammonium compounds, the latter two being represented generally by the formula $R'_4X^+$ wherein "X" is nitrogen or phosphorus and each R' is an alkyl, aryl, alkylaryl, or araalkyl group; wherein R' preferably contains from 1 to 8 carbon atoms or higher when R' is alkyl and greater than 6 carbon atoms when R' is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and tri-amines, including mixed amines, may also be employed as templates either alone or in combination with a quaternary ammonium compound or another template. The exact relationship of various templates when concurrently employed is not clearly understood. Mixtures of two or more templating agents can produce either mixtures of FeAPSOs or in the instance where one template is more strongly directing then another template the more strongly directing template may control the course of the hydrothermal crystallization wherein with the other template serving primarily to establish the pH conditions of the reaction mixture.

Representative templates include: tetramethylammonium; tetraethylammonium; tetrapropylammonium; tetrabutylammonium ions; tetrapentylammonium ions; di-n-propylamine; tripropylamine; triethylamine; triethanolamine; pyrrrolidine; cyclohexylamine; 2-methylpyridine; N,N-dimethylbenzylamine; N,N-diethylethanolamine; dicyclohexylamine; N,N-dimethylethanolamine; 1,4-diazabicyclo(2,2,2)octane; N-methyldiethanolamine, N-methyl-ethanolamine; N-methylcyclohexylamine; 3-methyl-pyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. As will be readily apparent from the illustrative examples set forth hereinafter, not every template will produce every FeAPSO composition although a single template can, with proper selection of the reaction conditions, cause the formation of different FeAPSO compositions, and a given FeAPSO composition can be produced using different templates.

In those instances where an alkoxide is the reactive iron, aluminum, phosphorus or silicon source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the FeAPSOs, although such may be acting as templates.

Alkali or other metal cations if present in the reaction mixture may facilitate the crystallization of certain FeAPSO species, although the exact function of such cations, when present, in crystallization, if any, is not presently known. Alkali cations present in the reaction mixture generally appear in the formed FeAPSO composition, either as occluded (extraneous) cations and/or as structural cations balancing net negative charges at various sites in the crystal lattice. It should be understood that although the unit formula for the FeAPSOs does not specifically recite the presence of alkali cations they are not excluded in the same sense that hydrogen cations and/or hydroxyl groups are not specifically provided for in the traditional formulae for zeolitic aluminosilicates.

Most any reactive iron source may be employed herein which permits the formation in situ of reactive iron (II) and/or iron (III) ions. The preferred reactive iron sources include iron salts, oxides, hydroxides, sulfate, acetate, nitrate and the like. Other sources such as freshly precipitated iron oxide, $\gamma$-FeOOH, are also suitable.

Most any reactive phosphorus source may be employed. Phosphoric acid is the most suitable phosphorus source employed to date. Accordingly, other acids of phosphorus are generally believed to be suitable phosphorus sources for use herein. Organic phosphates such as triethyl phosphate have been found satisfactory, and so also have crystalline or amorphous aluminophosphates such as the $AlPO_4$ compositions of U.S. Pat. No. 4,310,440. Organo-phosphorus compounds, such as tetrabutyl-phosphonium bromide have not, apparently, served as reactive sources of phosphorus, but these compounds do function as templating agents and may also be capable of being suitable phosphorus sources under proper process conditions (yet to be ascertained). Organic phosphorus compounds, e.g. esters, are believed to be generally suitable since they can generate acids of phosphorus in situ. Conventional phosphorus salts, such as sodium metaphosphate, may be used, at least in part as the phosphorus source, but they are not preferred.

Most any reactive aluminum source may be employed herein. The preferred reactive aluminum sources include aluminum alkoxides, such as aluminum isopropoxide, and pseudoboehmite. Crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but is generally not preferred.

Most any reactive silicon source may be employed such that $SiO_2$ tetrahedral units are formed in situ. The reactive silicon source may be silica in the form of a silica sol or as fumed silica, or other conventional sources of silica used in zeolite synthesis such as a reactive solid amorphous precipitated silica, silica gel, alkoxides of silicon, silicic acid, alkali metal silicates and the like.

The FeAPSO compositions of the present invention may exhibit cation-exchange capacity when analyzed using ion-exchange techniques heretofore employed with zeolite aluminosilicates and have pore diameters which are inherent in the lattice structure of each species and which are at least about 3 Å in diameter. Ion exchange of FeAPSO compositions will ordinarily be possible only after the organic moiety present as a result of synthesis has been removed from the pore system. Dehydration to remove water present in the as-synthesized FeAPSO compositions can usually be accomplished, to some degree at least, in the usual manner without removal of the organic moiety, but the absence of the organic species greatly facilitates adsorption and desorption procedures. The FeAPSO compositions will have various degrees of hydrothermal and thermal stability, some being quite remarkable in this regard, and will function as molecular sieve adsorbents, hydrocarbon conversion catalysts or catalyst bases.

In each example a stainless steel reaction vessel is utilized and is lined with an inert plastic material, polytetrafluoroethylene, to avoid contamination of the reaction mixture. In general, the final reaction mixture from which each FeAPSO composition is crystallized is prepared by forming mixtures of less than all of the reagents and thereafter incorporating into these mixtures additional reagents either singly or in the form of other intermediate mixtures of two or more reagents. In some instances the admixed reagents retain their identity in the intermediate mixture and in other cases some or all of the reagents are involved in chemical reactions to produce new reagents. The term "mixture" is applied in both cases. Further, unless otherwise specified each intermediate mixture as well as the final reaction mixture was stirred until substantially homogeneous.

X-ray analysis of reaction products are obtained by X-ray analysis using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\theta$ where $\theta$ is the Bragg angle as observed on the strip chart. Intensities are determined from the heights of diffraction peaks after subtracting background, "$I_o$" being the intensity of the strongest line or peak, and "I" being the intensity of each of the other peaks. Alternatively, the X-ray patterns are obtained from the copper K-alpha radiation by use of computer based techniques using Siemens D-500 X-ray powder diffractometers and Siemens Type K-805 X-ray sources, available from Siemens Corporation, Cherry Hill, N.J., with appropriate computer interface.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the composition of the prior art. In some of the X-ray patterns reported, the relative intensities of the d-spacings are indicated by the notations vs, s, m, m, w and vw which represent very strong, strong, medium, weak nd very weak, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A through K, wherein said x-ray patterns are for both the as-synthesized and calcined forms unless otherwise noted:

TABLE A

| | (FeAPSO-5) | |
| --- | --- | --- |
| $2\theta$ | d(Å) | Relative Intensity |
| 7.3–7.5 | 12.11–11.79 | m–vs |
| 14.8–14.95 | 5.99–5.93 | w–m |
| 19.6–19.8 | 4.53–4.48 | m |
| 21.0–21.2 | 4.23–4.19 | m |
| 22.35–22.5 | 3.98–3.95 | m–vs |
| 25.8–25.95 | 3.453–3.434 | w–m |

TABLE B

| | (FeAPSO-11) | |
| --- | --- | --- |
| $2\theta$ | d(Å) | Relative Intensity |
| 8.05–8.1 | 10.98–10.92 | m–s |
| 9.4–9.5 | 9.41–9.31 | m |
| 21.0–21.3 | 4.23–4.17 | vs |
| 22.1–22.4 | 4.022–3.969 | m–s |
| 22.65–23.1 | 3.926–3.850 | vw–m |
| | 3.850–3.802 | m–s |

TABLE C

| | (FeAPSO-16) | |
|---|---|---|
| 2θ | d(Å) | Relative Intensity |
| 11.3–11.4 | 7.83–7.76 | m |
| 18.55–18.75 | 4.78–4.73 | m |
| 21.85–22.0 | 4.07–4.04 | vs |
| 26.45–26.6 | 3.370–3.351 | w–m |
| 29.6–29.8 | 3.018–2.998 | w–m |

TABLE D

| | (FeAPSO-20) | |
|---|---|---|
| 2θ | d(Å) | Relative Intensity |
| 13.95–14.0 | 6.34–6.33 | m–vs |
| 19.8–20.0 | 4.48–4.44 | m |
| 24.3–24.5 | 3.667–3.663 | m–vs |
| 28.15–28.4 | 3.169–3.143 | w |
| 31.6–31.7 | 2.831–2.823 | w |
| 34.7–34.8 | 2.585–2.578 | w |

TABLE E

| | (FeAPSO-31) | |
|---|---|---|
| 2θ | d(Å) | Relative Intensity |
| 8.5–8.6 | 10.40–10.28 | w–s |
| 20.2–20.4 | 4.40–4.35 | m |
| 21.1–21.2 | 4.21–4.19 | w |
| 22.0–22.1 | 4.040–4.022 | m |
| 22.6–22.7 | 3.934–3.917 | vs |
| 31.7–31.9 | 2.822–2.805 | w–m |

TABLE F

| | (FeAPSO-34) | |
|---|---|---|
| 2θ | d(Å) | Relative Intensity |
| 9.35–9.7 | 9.46–9.12 | vs |
| 12.7–13.0 | 6.97–6.81 | w–m |
| 15.9–16.2 | 5.57–5.47 | w–m |
| 20.4–20.9 | 4.35–4.25 | w–s |
| 22.3–22.5 | 3.99–3.95 | vw–s |
| 25.7–26.2 | 3.466–3.401 | vw–m |

TABLE G

| | (FeAPSO-35) | |
|---|---|---|
| 2θ | d(Å) | Relative Intensity |
| 10.9–11.1 | 8.12–7.97 | vw–m |
| 13.2–13.5 | 6.71–6.56 | vw–w |
| 17.2–17.4 | 5.16–5.10 | w–m |
| 21.85–22.0 | 4.07–4.04 | vs |
| 23.2–23.8 | 3.834–3.739 | vw–m |
| 32.0–32.25 | 2.797–2.776 | vw–m |

TABLE H

| | (FeAPSO-36) | |
|---|---|---|
| 2θ | d(Å) | Relative Intensity |
| 7.45–8.0 | 11.14–11.05 | vs |
| 8.105–8.3 | 10.9084–10.65 | w–m |
| 16.3–16.6 | 5.44–5.34 | w–m |
| 18.9–19.414 | 4.70–4.5721 | w–m |
| 20.7–21.0 | 4.29–4.23 | w–m |

TABLE J

| | (FeAPSO-44) | |
|---|---|---|
| 2θ | d(Å) | Relative Intensity |
| 9.5 | 9.31 | m |
| 12.95 | 6.83 | m |
| 16.15 | 5.49 | vw |
| 21.0 | 4.23 | vs |
| 24.5 | 3.631 | m |

TABLE J-continued

| | (FeAPSO-44) | |
|---|---|---|
| 2θ | d(Å) | Relative Intensity |
| 30.9 | 2.894 | w |

TABLE K

| | (FeAPSO-46) | |
|---|---|---|
| 2θ | d(Å) | Relative Intensity |
| 6.6–6.8 | 13.39–13.00 | vw |
| 7.8–8.0 | 11.33–11.05 | vs |
| 13.2–13.6 | 6.71–6.51 | vw |
| 21.65–22.2 | 4.10–4.00 | vw |
| 22.9–23.45 | 3.883–3.793 | vw |
| 26.95–27.6 | 3.308–3.232 | vw |

The following examples are provided to further illustrate the invention and are not intended to be limiting thereof:

PREPARATIVE EXAMPLES

In the following examples the FeAPSO compositions were prepared using numerous reagents. The reagents employed and abbreviations employed herein, if any, for such reagents are as follows:

(a) Alipro: aluminum isopropoxide, $Al(OCH(CH_3)_2)_3$;

(b) LUDOX-LS: LUDOX-LS is the trademark of Du Pont for an aqueous solution of 30 weight percent $SiO_2$ and 0.1 weight percent $Na_2O$;

(c) CATAPAL: trademark for hydrated aluminum oxide containing about 75 wt. % $Al_2O_3$ (pseudoboehmite phase) and about 25 wt. percent water.

(c) $Fe(Ac)_2$: Iron (II) acetate;

(d) $FeSO_4$: Iron (II) sulfate hexahydrate;

(e) $H_3PO_4$: 85 weight percent phosphoric acid in water;

(f) TEAOH: 40 weight percent aqueous solution of tetraethylammonium hydroxide;

(g) TBAOH: 40 weight percent aqueous solution of tetrabutylammonium hydroxide;

(h) $Pr_2NH$: di-n-propylamine $(C_3H_7)_2NH$);

(i) $Pr_3N$: tri-n-propylamine $((C_3H_7)_3N)$;

(j) Quin: Quinuclidine $(C_7H_{13}N)$;

(k) MQuin: Methyl Quinuclidine hydroxide $(C_7H_{13}NCH_3OH)$;

(l) TMAOH: tetramethylammonium hydroxide pentahydrate; and (m) C-hex; cyclohexylamine.

EXAMPLES 1 TO 16

(a) Examples 1 to 8 were carried out to demonstrate the preparation of FeAPSO-34 and FeAPSO-5. The reaction mixtures were prepared by grinding the aluminum iso-propoxide in a blender followed by slowly adding the $H_3PO_4$ solution with mixing. A solution dispersion of iron acetate in water was added to the above mixture and then the LUDOX-LS was added. The organic templating agent was then added to this mixture, or in some cases one-half of this mixture, and the mixture blended to form a homogeneous mixture. The number of moles of each component in the reaction mixture was as follows:

| Component | Moles |
|---|---|
| $Al_2O_3$ | 0.9 |
| $P_2O_5$ | 0.9 |
| $SiO_2$ | 0.2** |
| FeO* | 0.2 |

-continued

| Component | Moles |
|---|---|
| TEAOH | 1.0 |
| H$_2$O | 50 |

*Iron (II) acetate reported as Iron (II) oxide.
**SiO$_2$ was 0.6 in examples 5 to 8.

Each reaction mixture was sealed in a stainless steel pressure vessel lined with polytetrafluoroethylene and heated in an oven at a temperature (see Table I), time (see Table I) and at the autogeneous pressure. The solid reaction product was recovered by filtration, washed with water and dried at room temperature. The products were analyzed and the observed FeAPSO products reported in Table I.

(b) Examples 9 to 16 were carried out to demonstrate the preparation of FeAPSO-11 and FeAPSO-5. The reaction mixtures were prepared by grinding the aluminum iso-propoxide in a blender followed by addition of a solution/dispersion of Iron (II) acetate. H$_3$PO$_4$ was added to this mixture and the resulting mixture blended to form a homogeneous mixture. LUDOX was added to this mixture except that in examples 13 to 16 the LUDOX was added with the H$_3$PO$_4$. The resulting mixtures were blended until a homogeneous mixture was observed. Organic templating agent was added to each mixture and the resulting mixtures placed in a stainless steel pressure vessel lined with polytetrafluoroethylene and heated, washed and the product recovered as in part (a) of this example. The products were analyzed and the observed FeAPSO products reported in Table I. The number of moles of each component in the reaction mixture was as follows:

| Component | Moles |
|---|---|
| Al$_2$O$_3$ | 0.9 |
| P$_2$O$_5$ | 0.9 |
| SiO$_2$ | 0.2 |
| FeO* | 0.2 |
| Template | 1.0 |
| H$_2$O | 50 |

*Iron (II) acetate reported as Iron (II) oxide.

(c) Two reaction mixtures, designated Examples A and B in Table I, did not show FeAPSO products when analyzed by X-ray. Examples A and B followed the same procedure employed for Examples 5 and 6.

TABLE I

| Example | Template | Temp (°C.) | Time (hr.) | FeAPSO Product[1] |
|---|---|---|---|---|
| 1 | TEAOH | 150 | 64 | FeAPSO-34; FeAPSO-5 |
| 2 | TEAOH | 150 | 158 | FeAPSO-34; FeAPSO-5 |
| 3 | TEAOH | 200 | 64 | FeAPSO-34; FeAPSO-5 |
| 4 | TEAOH | 200 | 158 | FeAPSO-34; FeAPSO-5 |
| 5 | TEAOH | 150 | 40 | FeAPSO-34; FeAPSO-5 |
| 6 | TEAOH | 150 | 161 | FeAPSO-34; FeAPSO-5 |
| 7 | Pr$_2$NH | 150 | 50 | FeAPSO-11 |
| 8 | Pr$_2$NH | 150 | 168 | FeAPSO-11 |
| 9 | Pr$_2$NH | 200 | 50 | FeAPSO-11 |
| 10 | Pr$_2$NH | 200 | 168 | FeAPSO-11 |
| 11 | Pr$_3$N | 150 | 50 | FeAPSO-5 |
| 12 | Pr$_3$N | 150 | 168 | FeAPSO-5 |
| 13 | Pr$_3$N | 200 | 50 | FeAPSO-5 |
| 14 | Pr$_3$N | 200 | 168 | FeAPSO-5 |
| A | TEAOH | 100 | 40 | — |
| B | TEAOH | 100 | 161 | — |

[1]Major species as identified by x-ray powder diffraction pattern of product, except that when two species were identified the first species listed is the major species observed. A "—" indicates no FeAPSO product was present as determined by X-ray analysis.

EXAMPLES 15 TO 19

Examples 15 to 19 were carried out according to the general preparative procedure employed for examples 7 to 14 with examples 15 to 18 following the procedure employed for examples 7 to 10 and example 19 following the procedure followed for examples 11 to 14. The reactive source of iron was Iron (II) sulfate instead of Iron (II) acetate. The temperature and time for the crystallization (digestion) procedure are set forth in Table II.

The number of moles of each component in the reaction mixtures for examples 15 to 18 was as follows:

| Component | Moles |
|---|---|
| Al$_2$O$_3$ | 0.9 |
| P$_2$O$_5$ | 0.9 |
| SiO$_2$ | 0.6 |
| FeO* | 0.2 |
| Pr$_3$N | 1.5 |
| H$_2$O | 50 |

*Iron (II) sulfate reported as Iron (II) oxide.

The number of moles of each component in the reaction mixture of example 19 was as follows:

| Component | Moles |
|---|---|
| Al$_2$O$_3$ | 0.9 |
| P$_2$O$_5$ | 0.9 |
| SiO$_2$ | 0.2 |
| FeO* | 0.2 |
| Pr$_3$N | 1.0 |
| H$_2$O | 50 |

*Iron (II) sulfate reported as Iron (II) oxide.

The products were subjected to analysis by x-ray and the observed FeAPSO products reported in Table II.

TABLE II

| Example | Template | Temp (°C.) | Time (hr.) | FeAPSO Product[1] |
|---|---|---|---|---|
| 15 | Pr$_3$N | 150 | 48 | FeAPSO-5 |
| 16 | Pr$_3$N | 150 | 160 | FeAPSO-5 |
| 17 | Pr$_3$N | 200 | 48 | FeAPSO-5 |
| 18 | Pr$_3$N | 200 | 160 | FeAPSO-5 |
| 19 | Pr$_3$N | 200 | 72 | FeAPSO-5 |

[1]Major species as identified by x-ray powder diffraction pattern of product, except that when two species were identified the first species listed is the major species observed.

EXAMPLES 20-27

Examples 20-27 were carried out according to the general preparative procedure employed for examples 1 to 8 using the following number of moles of each component in the reaction mixture:

| Component | Moles |
|---|---|
| Al$_2$O$_3$ | 0.9 |
| P$_2$O$_5$ | 0.9 |

-continued

| Component | Moles |
|---|---|
| SiO₂* | 0.2, 0.6 |
| FeO** | 0.2 |
| Template | 1.0 |
| H₂O | 50 |

*0.2 moles in examples 20 to 23 and 0.6 moles in examples 24 to 27
**Iron (II) acetate reported as Iron (II) oxide.

The temperature and time for the crystallization procedure and the observed FeAPSO products are reported in Table III.

TABLE III

| Example | Template | Temp (°C.) | Time (hr.) | FeAPSO Product[1] |
|---|---|---|---|---|
| 20 | Quin | 150 | 64 | FeAPSO-16 |
| 21 | Quin | 150 | 158 | FeAPSO-16; FeAPSO-35 |
| 22 | Quin | 200 | 64 | FeAPSO-16; FeAPSO-35 |
| 23 | Quin | 200 | 158 | FeAPSO-16; FeAPSO-35 |
| 24 | MQuin | 100 | 49 | FeAPSO-16 |
| 25 | MQuin | 100 | 161 | FeAPSO-16 |
| 26 | MQuin | 150 | 49 | FeAPSO-16; FeAPSO-35 |
| 27 | MQuin | 150 | 161 | FeAPSO-16; FeAPSO-35 |

[1]Major species as identified by x-ray powder diffraction pattern of product, except that when two species were identified the first species listed is the major species observed.

EXAMPLES 28 AND 29

Examples 28 and 29 were carried out according to the procedure of examples 13 to 16, except that iron (II) sulfate, was employed as the reactive iron source instead of iron (II) acetate. The number of moles of each component in the reaction mixture for each example was as follows:

| Component | Moles |
|---|---|
| Al₂O₃ | 0.8 |
| P₂O₅ | 1.0 |
| SiO₂ | 0.4 |
| FeO* | 0.4 |
| Template | 2.0 |
| H₂O | 83 |

*Iron (II) sulfate reported here as FeO

Examples C and D followed the procedure for Examples 28 and 29. X-ray analysis of the reaction products did not show FeAPSO products.

The temperature and time for the crystallization procedure and the observed FeAPSO products are reported in Table IV.

TABLE IV

| Example | Template | Temp (°C.) | Time (hr.) | FeAPSO Product[1] |
|---|---|---|---|---|
| 28 | TBAOH | 200 | 49 | FeAPSO-5 |
| 29 | TBAOH | 200 | 161 | FeAPSO-5 |
| C | TBAOH | 150 | 49 | — |
| D | TBAOH | 150 | 161 | — |

[1]Major species as identified by x-ray powder diffraction pattern of product, except that when two species were identified the first species listed is the major species observed. A "—" indicates no FeAPSO product was present as determined by X-ray analysis.

EXAMPLES 30 TO 43

Examples 30 to 43 were carried out according to the procedure employed for examples 1 to 8 except that in examples 30 and 31 the aluminum source was CATAPAL and in examples 33 to 36 and 43 a seed crystal of a topologically similar molecular sieve was employed. The number of moles of each component in the reaction mixture in examples 30 to 43 was:

| Component | Moles |
|---|---|
| Al₂O₃ | 0.9 |
| P₂O₅ | 0.9 |
| SiO₂ | 0.2** |
| FeO* | 0.2 |
| Template | 1.0** |
| H₂O | 50 |

*Iron (II) acetate reported here as FeO
**SiO₂ was 0.6 in example 32 and was 2.0 moles of template in examples 37 to 40.

The template, temperature, time for the crystallization procedure and the observed FeAPSO products are reported in Table V.

TABLE V

| Example | Template | Temp (°C.) | Time (hr.) | FeAPSO Product(s)[1] |
|---|---|---|---|---|
| 30 | TMAOH | 150 | 42 | FeAPSO-20 |
| 31 | TMAOH | 150 | 132 | FeAPSO-20 |
| 32 | C-hex | 220 | 114 | FeAPSO-5; FeAPSO-44 |
| 33 | Pr₂NH | 150 | 47 | FeAPSO-31 |
| 34 | Pr₂NH | 150 | 182 | FeAPSO-31 |
| 35 | Pr₂NH | 200 | 47 | FeAPSO-31 |
| 36 | Pr₂NH | 200 | 158 | FeAPSO-31 |
| 37 | Pr₂NH | 150 | 182 | FeAPSO-46 |
| 38 | Pr₂NH | 150 | 182 | FeAPSO-46 |
| 39 | Pr₂NH | 150 | 47 | FeAPSO-5; FeAPSO-34 |
| 40 | Pr₂NH | 200 | 158 | FeAPSO-11; FeAPSO-31 |
| 41 | Pr₃N | 150 | 42 | FeAPSO-5 |
| 42 | Pr₃N | 150 | 132 | FeAPSO-5 |
| 43 | Pr₃N | 150 | 42 | FeAPSO-5 |
| E | Pr₂NH | 150 | 47 | — |

[1]Major species as identified by x-ray powder diffraction pattern of product, except that when two species were identified the first species listed is the major species observed. A "—" indicates no FeAPSO product was present as determined by X-ray analysis.

EXAMPLE 44

(a) Samples of FeAPSO products were calcined at 600° C. in air for 2 hours to remove at least part of the organic templating agent, except that FeAPSO-5 and FeAPSO-11 were calcined for 2.25 hours. The example in which the FeAPSO was prepared is indicated in parenthesis. The adsorption capacities of each calcined sample were measured using a standard McBain-Bakr gravimetric adsorption apparatus. The samples were activated in a vacuum at 350° C. prior to measurement. The McBain-Bakr data for the FeAPSO compositions are set forth hereinafter.

(b) FeAPSO-5 (example 12):

| Adsorbate | Kinetic Diameter, Å | Pressure (Torr) | Temp (°C.) | Wt. % Adsorbed |
|---|---|---|---|---|
| O₂ | 3.46 | 100 | −183 | 9.7 |
| O₂ | 3.46 | 734 | −183 | 11.6 |
| neopentane | 6.2 | 100 | 24.5 | 3.8 |
| cyclohexane | 6.0 | 59 | 23.7 | 5.7 |
| H₂O | 2.65 | 4.6 | 23.9 | 10.7 |
| H₂O | 2.65 | 20.0 | 23.6 | 19.2 |

The above data demonstrate that the pore size of the calcined product is greater than 6.2 Å.

(c) FeAPSO-11 (example 10):

| Adsorbate | Kinetic Diameter, Å | Pressure (Torr) | Temp (°C.) | Wt. % Adsorbed |
|---|---|---|---|---|
| O₂ | 3.46 | 100 | −183 | 7.6 |

-continued

| Adsorbate | Kinetic Diameter, Å | Pressure (Torr) | Temp (°C.) | Wt. % Adsorbed |
|---|---|---|---|---|
| $O_2$ | 3.46 | 734 | −183 | 9.2 |
| neopentane | 6.2 | 100 | 24.5 | 0.2 |
| cyclohexane | 6.0 | 59 | 23.7 | 4.2 |
| $H_2O$ | 2.65 | 4.6 | 23.9 | 10.8 |
| $H_2O$ | 2.65 | 20.0 | 23.6 | 16.7 |

The above data demonstrate that the pore size of the calcined product is about 6.0 Å.

(d) FeAPSO-20 (example 31):

| Adsorbate | Kinetic Diameter, Å | Pressure (Torr) | Temp (°C.) | Wt. % Adsorbed |
|---|---|---|---|---|
| $O_2$ | 3.46 | 99 | −183 | 1.5 |
| $O_2$ | 3.46 | 749 | −183 | 8.5 |
| $H_2O$ | 2.65 | 4.6 | 23.2 | 22.7 |
| $H_2O$ | 2.65 | 16.8 | 23.5 | 30.0 |

The above data demonstrates that the pore size of the calcined product is about 3.0 Å.

(e) FeAPSO-31 (example 34):

| Adsorbate | Kinetic Diameter, Å | Pressure (Torr) | Temp (°C.) | Wt. % Adsorbed |
|---|---|---|---|---|
| $O_2$ | 3.46 | 99 | −183 | 6.8 |
| $O_2$ | 3.46 | 749 | −183 | 11.6 |
| neopentane | 6.2 | 100 | 23.4 | 3.6 |
| cyclohexane | 6.0 | 57 | 23.4 | 6.9 |
| $H_2O$ | 2.65 | 4.6 | 23.2 | 6.5 |
| $H_2O$ | 2.65 | 16.8 | 23.5 | 21.3 |

The above data demonstrates that the pore size of the calcined product is greater than about 6.2 Å.

(f) FeAPSO-46 (example 38):

| Adsorbate | Kinetic Diameter, Å | Pressure (Torr) | Temp (°C.) | Wt. % Adsorbed |
|---|---|---|---|---|
| $O_2$ | 3.46 | 100 | −183 | 2.6 |
| $O_2$ | 3.46 | 749 | −183 | 11.7 |
| neopentane | 6.2 | 100 | 23.4 | 1.1 |
| cyclohexane | 6.0 | 57 | 23.4 | 6.4 |
| $H_2O$ | 2.65 | 4.6 | 23.2 | 7.2 |
| $H_2O$ | 2.65 | 16.8 | 23.5 | 13.0 |

The above data demonstrates that the pore size of the calcined product is greater than about 6.2 Å.

EXAMPLE 45

Samples of FeAPSO products were subjected to chemical analysis as follows:

(a) The chemical analysis for FeAPSO-5 (example 12) was:

| Component | Weight Percent |
|---|---|
| $Al_2O_3$ | 32.2 |
| $P_2O_5$ | 45.4 |
| FeO | 4.7 |
| $SiO_2$ | 1.9 |
| Carbon | 4.9 |
| LOI* | 14.6 |

*LOI = Loss on Ignition

The above chemical analysis gives an overall product composition in molar oxide ratios (anhydrous basis) of: $0.14R:0.21FeO$; $1.0Al_2O_3:1.01P_2O_5:0.10SiO_2$; and a formula (anhydrous basis) of:

$$0.03R(Fe_{0.05}Al_{0.46}P_{0.47}Si_{0.02})O_2$$

(b) The chemical analysis of FeAPSO-11 (example 10) was:

| Component | Weight Percent |
|---|---|
| $Al_2O_3$ | 33.2 |
| $P_2O_5$ | 48.8 |
| FeO | 4.5 |
| $SiO_2$ | 2.4 |
| Carbon | 5.1 |
| LOI* | 9.8 |

*LOI = Loss on Ignition

The above chemical analysis gives an overall product composition in molar oxide ratios (anhydrous basis) of: $0.22R:0.19FeO$; $1.0Al_2O_3$; $1.06P_2O_5$; $0.08SiO_2$; and a formula (anhydrous basis) of: $0.05(Fe_{0.04}Al_{0.45}P_{0.48}Si_{0.03})O_2$ (c) The chemical analysis of FeAPSO-20 (example 31) was:

| Component | Weight Percent |
|---|---|
| $Al_2O_3$ | 29.1 |
| $P_2O_5$ | 42.0 |
| FeO | 4.8 |
| $SiO_2$ | 2.5 |
| Carbon | 7.6 |
| LOI* | 19.7 |

*LOI = Loss on Ignition

The above chemical analysis gives an overall product composition in molar oxide ratios (anhydrous basis) of: $0.55R:0.23FeO$; $1.0Al_2O_3$; $1.04P_2O_5$; $0.15SiO_2$; and a formula (anhydrous basis) of: $0.12(Fe_{0.05}Al_{0.45}P_{0.47}Si_{0.03})O_2$ (d) The chemical analysis of FeAPSO-31 (example 34) was:

| Component | Weight Percent |
|---|---|
| $Al_2O_3$ | 34.7 |
| $P_2O_5$ | 45.3 |
| FeO | 4.2 |
| $SiO_2$ | 1.6 |
| Carbon | 3.4 |
| LOI* | 12.9 |

*LOI = Loss on Ignition

The above chemical analysis gives an overall product composition in molar oxide ratios (anhydrous basis) of: $0.14R:0.17FeO$; $1.0Al_2O_3$; $0.94P_2O_5$; $0.08SiO_2$; and a formula (anhydrous basis) of: $0.03(Fe_{0.04}Al_{0.49}P_{0.45}Si_{0.02})O_2$

EXAMPLE 46

EDAX (energy dispersive analysis by x-ray) microprobe analysis in conjunction with SEM (scanning electron microscope) was carried out on clear crystals of FeAPSO products of the hereinafter designated examples. Analysis of crystals having a morphology characteristic of FeAPSO-5, FeAPSO-11, FeAPSO-20, FeAPSO-31, FeAPSO-34 and FeAPSO-46 gave the following analysis based on relative peak heights:

(a) FeAPSO-5 (example 12):

|  | Average of Spot Probes |
|---|---|
| Fe | 0.02 |
| Al | 0.44 |
| P | 0.52 |
| Si | 0.02 |

(b) FeAPSO-11 (example 10):

|  | Average of Spot Probes |
|---|---|
| Fe | 0.03 |
| Al | 0.42 |
| P | 0.52 |
| Si | 0.03 |

(c) FeAPSO-20 (example 31):

|  | Average of Spot Probes |
|---|---|
| Fe | 0.04 |
| Al | 0.42 |
| P | 0.49 |
| Si | 0.05 |

(d) FeAPSO-31 (example 34):

|  | Average of Spot Probes |
|---|---|
| Fe | 0.01 |
| Al | 0.44 |
| P | 0.48 |
| Si | 0.06 |

(e) FeAPSO-34 (example 3):

|  | Average of Spot Probes |
|---|---|
| Fe | 0.04 |
| Al | 0.43 |
| P | 0.45 |
| Si | 0.07 |

(f) FeAPSO-46 (example 38):

|  | Average of Spot Probes |
|---|---|
| Fe | 0.05 |
| Al | 0.40 |
| P | 0.43 |
| Si | 0.12 |

EXAMPLE 47

(a) FeAPSO-5, as prepared in example 12, was subjected to x-ray analysis. FeAPSO-5 was determined to have a characteristic x-ray powder diffraction pattern which contains the d-spacings set forth below:

TABLE V

| $2\theta$ | d, (Å) | 100 × I/Io |
|---|---|---|
| 7.4 | 11.95 | 100 |
| 8.0* | 11.05 | 4 |
| 12.6* | 7.03 | 13 |
| 13.0 | 6.81 | 7 |
| 14.95 | 5.93 | 15 |
| 16.0* | 5.54 | <1 |
| 16.5* | 5.37 | 1 |
| 17.1* | 5.19 | 1 |
| 18.4* | 4.82 | <1 |
| 19.8 | 4.48 | 33 |
| 20.3* | 4.37 | 5 |
| 21.1 | 4.21 | 27 |
| 22.0* | 4.04 | sh |
| 22.4 | 3.969 | 38 |
| 22.6* | 3.934 | sh |
| 24.7 | 3.604 | 2 |
| 25.1* | 3.548 | 1 |
| 25.9 | 3.440 | 15 |
| 27.2* | 3.278 | 1 |
| 28.0* | 3.187 | 2 |
| 28.4* | 3.143 | 1 |
| 29.0 | 3.079 | 6 |
| 30.0 | 2.979 | 19 |
| 31.8* | 2.814 | 3 |
| 33.7 | 2.660 | 2 |
| 34.5 | 2.600 | 9 |
| 35.2* | 2.550 | 1 |
| 37.0 | 2.564 | 1 |
| 37.8 | 2.380 | 4 |
| 41.6 | 2.171 | 1 |
| 42.3 | 2.137 | 2 |
| 42.9 | 2.108 | 1 |
| 43.6 | 2.076 | 1 |
| 45.0 | 2.015 | 1 |
| 45.7* | 1.985 | 1 |
| 47.7 | 1.907 | 3 |
| 51.5 | 1.774 | 1 |
| 55.6 | 1.653 | 1 |

*peak contains impurity (b) A portion of the as-synthesized FeAPSO-5 of part (a) was calcined in air at a temperature beginning at 500° C. and ending at 600° C. over a period of 2.25 hours. The calcined product was characterized by the x-ray powder diffraction pattern below:

| $2\theta$ | d, (Å) | 100 × I/Io |
|---|---|---|
| 7.4 | 11.95 | 100 |
| 7.9* | 11.19 | sh |
| 8.45* | 10.46 | 35 |
| 12.85 | 6.89 | 18 |
| 14.8 | 5.99 | 8 |
| 15.5* | 5.72 | 13 |
| 16.4* | 5.40 | 2 |
| 17.0* | 5.22 | 5 |
| 19.75 | 4.50 | 31 |
| 20.2* | 4.40 | 14 |
| 21.1 | 4.21 | 33 |
| 21.4* | 4.15 | sh |
| 22.0* | 4.04 | sh |
| 22.45 | 3.960 | 83 |
| 23.8* | 3.739 | 1 |
| 24.8 | 3.59 | 2 |
| 25.1* | 3.548 | 2 |
| 25.95 | 3.434 | 31 |
| 27.0* | 3.302 | 2 |
| 27.9* | 3.198 | 3 |
| 29.05 | 3.074 | 14 |
| 30.05 | 2.974 | 22 |
| 31.5* | 2.840 | 29 |
| 31.65 | 2.827 | 5 |
| 34.55 | 2.596 | 15 |
| 35.0* | 2.564 | 3 |
| 36.1* | 2.488 | 1 |
| 37.0 | 2.430 | 4 |
| 37.8 | 2.380 | 8 |
| 38.2* | 2.356 | 2 |
| 39.2* | 2.298 | 2 |
| 40.2* | 2.151 | 2 |
| 42.3 | 2.137 | 2 |
| 43.0 | 2.103 | 1 |
| 43.8 | 2.067 | 2 |
| 45.2 | 2.006 | 1 |
| 46.6* | 1.949 | 2 |
| 47.7 | 1.907 | 4 |
| 51.6 | 1.771 | 4 |

-continued

| 2θ | d, (Å) | 100 × I/Io |
|---|---|---|
| 55.6 | 1.653 | 2 |

*peak contains impurity (c) The FeAPSO-5 compositions are generally characterized by the data of Table VI below:

TABLE VI

| 2θ | d, (Å) | Relative Intensity |
|---|---|---|
| 7.3–7.5 | 12.11–11.79 | m–vs |
| 14.8–14.95 | 5.99–5.93 | w–m |
| 19.6–19.8 | 4.53–4.48 | m |
| 21.0–21.2 | 4.23–4.19 | m |
| 22.35–22.5 | 3.98–3.95 | m–vs |
| 25.8–25.95 | 3.453–3.434 | w–m |

(d) The FeAPSO-5 compositions for which x-ray powder diffraction data have been obtained have patterns which are characterized by the x-ray powder diffraction pattern shown in Table VII, below:

TABLE VII

| 2θ | d, (Å) | 100 × I/Io |
|---|---|---|
| 7.3–7.5 | 12.11–11.79 | 55–100 |
| 12.8–13.0 | 6.92–6.81 | 7–18 |
| 14.8–14.95 | 5.99–5.93 | 17–27 |
| 19.6–19.8 | 4.53–4.48 | 24–60 |
| 21.0–21.2 | 4.23–4.19 | 27–53 |
| 22.35–22.5 | 3.98–3.95 | 38–100 |
| 24.7–24.85 | 3.604–3.583 | 0–6 |
| 25.8–25.95 | 3.453–3.434 | 15–68 |
| 28.85–29.05 | 3.095–3.074 | 6–24 |
| 29.8–30.05 | 2.998–2.974 | 9–27 |
| 33.45–33.7 | 2.679–2.660 | 2–10 |
| 34.4–34.55 | 2.607–2.596 | 8–17 |
| 36.9–37.0 | 2.436–2.564 | 1–7 |
| 37.65–37.9 | 2.389–2.374 | 4–13 |
| 41.4–41.6 | 2.181–2.171 | 0–4 |
| 42.1–42.3 | 2.146–2.137 | 0–4 |
| 42.6–43.1 | 2.122–2.099 | 0–4 |
| 43.5–43.8 | 2.080–2.067 | 0–4 |
| 44.9–45.2 | 2.019–2.006 | 0–7 |
| 47.6–47.7 | 1.910–1.907 | 0–5 |
| 51.3–51.6 | 1.781–1.771 | 0–4 |
| 55.4–55.6 | 1.658–1.653 | 1–6 |

EXAMPLE 48

(a) FeAPSO-11, as prepared in example 10, was subjected to x-ray analysis. FeAPSO-11 was determined to have a characteristic x-ray powder diffraction pattern which contains the d-spacings set forth below:

| 2θ | d, (Å) | 100 × I/Io |
|---|---|---|
| 8.1 | 10.92 | 31 |
| 9.45 | 9.36 | 47 |
| 13.15 | 6.73 | 15 |
| 15.7 | 5.64 | 34 |
| 16.2 | 5.47 | 5 |
| 19.0 | 4.67 | 6 |
| 20.3 | 4.37 | 43 |
| 21.0 | 4.23 | 100 |
| 22.1 | 4.022 | 62 |
| 22.5* | 3.952 | sh |
| 22.65 | 3.926 | 61 |
| 23.1 | 3.850 | 86 |
| 24.7 | 3.604 | 10 |
| 26.4 | 3.376 | 25 |
| 28.2** | 3.164 | sh |
| 28.6 | 3.121 | 17 |
| 29.0 | 3.079 | sh |
| 29.5 | 3.028 | 7 |
| 31.5 | 2.840 | 9 |

-continued

| 2θ | d, (Å) | 100 × I/Io |
|---|---|---|
| 32.7 | 2.755 | 19 |
| 33.6** | 2.667 | 2 |
| 34.1 | 2.629 | 9 |
| 36.3 | 2.415 | 6 |
| 37.7 | 2.386 | 14 |
| 39.2 | 2.298 | 5 |
| 42.9 | 2.108 | 5 |
| 44.7 | 2.027 | 6 |
| 50.6 | 1.804 | 5 |
| 54.7 | 1.678 | 5 |
| 55.5 | 1.656 | 3 |

*peak may contain impurity
**impurity peak (b) A portion of the as-synthesized FeAPSO-11 of part (a) was calcined in air at 600° C. for about 2.25 hours. The calcined product was characterized by the x-ray powder diffraction pattern below:

| 2θ | d, (Å) | 100 × I/Io |
|---|---|---|
| 8.05 | 10.98 | 60 |
| 9.5 | 9.31 | 72 |
| 12.9** | 6.86 | sh |
| 13.1 | 6.76 | 20 |
| 13.7** | 6.46 | 3 |
| 14.7** | 6.03 | 3 |
| 15.9 | 5.57 | 55 |
| 16.1 | 5.51 | sh |
| 17.6** | 5.04 | 3 |
| 19.9** | 4.46 | sh |
| 20.3 | 4.37 | 28 |
| 21.3 | 4.17 | 100 |
| 21.9* | 4.06 | sh |
| 22.4 | 3.969 | 88 |
| 23.0* | 3.867 | sh |
| 23.4 | 3.802 | 70 |
| 24.0** | 3.708 | 3 |
| 24.4** | 3.648 | 5 |
| 25.0 | 3.562 | 4 |
| 25.8* | 3.453 | 7 |
| 26.5 | 3.363 | 20 |
| 27.7** | 3.220 | 5 |
| 29.0 | 3.079 | sh |
| 29.6 | 3.018 | 20 |
| 30.4* | 2.940 | 7 |
| 31.8 | 2.814 | 10 |
| 32.7 | 2.739 | 18 |
| 34.1 | 2.629 | 5 |
| 34.5** | 2.600 | 4 |
| 35.6* | 2.522 | 4 |
| 36.2 | 2.481 | 4 |
| 38.0 | 2.368 | 10 |
| 43.3 | 2.090 | 3 |
| 44.8 | 2.023 | 5 |
| 49.0* | 1.859 | 3 |
| 49.6* | 1.838 | 3 |
| 54.6 | 1.681 | 3 |
| 55.7* | 1.650 | 3 |

*peak may contain impurity
**impurity peak (c) The FeAPSO-11 compositions are generally characterized by the data of Table VIII below:

TABLE VIII

| 2θ | d, (Å) | Relative Intensity |
|---|---|---|
| 8.05–8.1 | 10.98–10.92 | m–s |
| 9.4–9.5 | 9.41–9.31 | m |
| 21.0–21.3 | 4.23–4.17 | vs |
| 22.1–22.4 | 4.022–3.969 | m–s |
| 22.65–23.1 | 3.926–3.850 | vw–m |
| 23.1–23.4 | 3.850–3.802 | m–s |

(d) The FeAPSO-11 compositions for which x-ray powder diffraction data have been obtained have patterns which are characterized by the x-ray powder diffraction pattern shown in Table IX, below:

TABLE IX

| 2θ | d, (Å) | 100 × I/Io |
|---|---|---|
| 8.05–8.1 | 10.98–10.92 | 30–80 |
| 9.4–9.5 | 9.41–9.31 | 47–78 |
| 13.05–13.2 | 6.78–6.71 | 13–24 |
| 15.7–15.9 | 5.64–5.57 | 33–54 |
| 16.15–16.3 | 5.49–5.44 | 0–6 |
| 18.9–19.05 | 4.70–4.66 | 0–6 |
| 20.2–20.4 | 4.40–4.35 | 30–43 |
| 21.0–21.3 | 4.23–4.17 | 100 |
| 21.9 | 4.06 | sh |
| 22.1–22.4 | 4.022–3.969 | 54–86 |
| 22.5–22.6 | 3.952–3.934 | sh |
| 22.65–23.1 | 3.926–3.850 | sh–61 |
| 23.1–23.4 | 3.850–3.802 | 48–86 |
| 24.4–24.5 | 3.648–3.633 | sh–6 |
| 24.7–24.9 | 3.604–3.576 | 0–10 |
| 26.4–26.5 | 3.376–3.363 | 15–25 |
| 28.6–28.8 | 3.121–3.100 | 17–19 |
| 28.9–29.0 | 3.079–3.089 | sh |
| 29.5–29.6 | 3.028–3.018 | 7–21 |
| 31.5–31.8 | 2.840–2.814 | 8–12 |
| 32.7–32.85 | 2.755–2.726 | 13–19 |
| 34.1–34.25 | 2.629–2.618 | 5–9 |
| 36.2–36.5 | 2.481–2.462 | 5–7 |
| 37.6–38.0 | 2.392–2.368 | 7–14 |
| 39.2–39.4 | 2.298–2.287 | 2–5 |
| 42.9–43.2 | 2.108–2.094 | 3–5 |
| 44.7–44.9 | 2.027–2.019 | 3–6 |
| 48.3–48.4 | 1.884–1.881 | 0–2 |
| 50.5–50.9 | 1.807–1.794 | 0–5 |
| 54.5–54.8 | 1.684–1.675 | 0–5 |
| 55.4–55.6 | 1.658–1.653 | 0–3 |

EXAMPLE 49

(a) FeAPSO-16, as prepared in example 21, was subjected to x-ray analysis. FeAPSO-16 was determined to have a characteristic x-ray powder diffraction pattern which contains the d-spacings set forth below:

| 2θ | d, (Å) | 100 × I/Io |
|---|---|---|
| 8.6** | 10.28 | 7 |
| 10.9** | 8.12 | sh |
| 11.3 | 7.83 | 58 |
| 13.2** | 6.71 | 8 |
| 15.8** | 5.61 | 2 |
| 17.25** | 5.14 | 21 |
| 17.7** | 5.01 | 2 |
| 18.65 | 4.76 | 40 |
| 20.3** | 4.37 | sh |
| 20.7** | 4.29 | sh |
| 21.1** | 4.21 | sh |
| 21.85 | 4.07 | 100 |
| 22.9 | 3.883 | 10 |
| 23.6** | 3.770 | 2 |
| 25.0** | 3.562 | 1 |
| 25.8** | 3.453 | 1 |
| 26.5 | 3.363 | 22 |
| 27.1 | 3.290 | sh |
| 28.6** | 3.121 | sh |
| 28.9 | 3.089 | 9 |
| 29.7 | 3.008 | 24 |
| 32.0** | 2.797 | 10 |
| 32.6 | 2.747 | 4 |
| 34.6* | 2.592 | 8 |
| 35.6** | 2.522 | 1 |
| 37.85 | 2.377 | 8 |
| 39.7 | 2.270 | 3 |
| 44.3 | 2.045 | 2 |
| 48.45* | 1.879 | 7 |
| 49.4** | 1.845 | 2 |
| 51.4** | 1.778 | 1 |
| 52.4 | 1.746 | 1 |

-continued

| 2θ | d, (Å) | 100 × I/Io |
|---|---|---|
| 54.8* | 1.675 | 2 |

*peak may contain impurity
**impurity peak (b) The FeAPSO-16 compositions are generally characterized by the data of Table X below:

TABLE X

| 2θ | d, (Å) | Relative Intensity |
|---|---|---|
| 11.3–11.4 | 7.83–7.76 | m |
| 18.55–18.75 | 4.78–4.73 | m |
| 21.85–22.0 | 4.07–4.04 | vs |
| 26.45–26.6 | 3.370–3.351 | w–m |
| 29.6–29.8 | 3.018–2.998 | w–m |

(c) The FeAPSO-16 compositions for which x-ray powder diffraction data have been obtained have patterns which are characterized by the x-ray powder diffraction pattern shown in Table XI, below:

TABLE XI

| 2θ | d, (Å) | 100 × I/Io |
|---|---|---|
| 11.3–11.4 | 7.83–7.76 | 38–63 |
| 18.55–18.75 | 4.78–4.73 | 31–63 |
| 21.85–22.0 | 4.07–4.04 | 100 |
| 22.9 | 3.883 | sh–10 |
| 26.45–26.6 | 3.370–3.351 | 18–26 |
| 28.9–29.0 | 3.089–3.079 | 0–13 |
| 29.6–29.8 | 3.018–2.998 | 17–30 |
| 32.4–32.8 | 2.763–2.730 | 0–13 |
| 34.5–34.6 | 2.600–2.592 | 0–10 |
| 37.65–37.9 | 2.389–2.374 | 0–10 |
| 39.5–39.7 | 2.281–2.270 | 0–6 |
| 44.1–44.5 | 2.054–2.036 | 0–6 |
| 48.2–48.5 | 1.888–1.877 | 0–8 |
| 52.0–52.4 | 1.759–1.746 | 0–3 |
| 54.4–54.8 | 1.687–1.675 | 0–3 |

EXAMPLE 50

(a) FeAPSO-20, as prepared to in example 31, was subjected to x-ray analysis. FeAPSO-20 was determined to have a characteristic x-ray powder diffraction pattern which contains the d-spacings set forth below:

| 2θ | d, (Å) | 100 × I/Io |
|---|---|---|
| 14.0 | 6.32 | 59 |
| 19.85 | 4.47 | 47 |
| 22.25 | 3.998 | 4 |
| 24.35 | 3.654 | 100 |
| 28.2 | 3.164 | 16 |
| 31.6 | 2.831 | 12 |
| 34.7 | 2.584 | 16 |
| 37.6 | 2.394 | 2 |
| 40.3 | 2.240 | 4 |
| 42.85 | 2.110 | 5 |
| 47.65 | 1.909 | 4 |
| 52.0 | 1.758 | 8 |

(b) A portion of the as-synthesized FeAPSO-20 of part (a) was calcined in air heating the sample from 500° C. to 600° C. over a period of 2 hours. The calcined product was characterized by the x-ray powder diffraction pattern below:

| 2θ | d, (Å) | 100 × I/Io |
|---|---|---|
| 7.05* | 12.56 | 6 |
| 7.5* | 11.82 | 6 |
| 14.05 | 6.31 | 100 |

| 2θ | d, (Å) | 100 × I/Io |
|---|---|---|
| 20.05 | 4.43 | 28 |
| 22.6 | 3.935 | 6 |
| 23.85* | 3.733 | 5 |
| 24.5 | 3.635 | 45 |
| 28.4 | 3.143 | 11 |
| 31.7 | 2.823 | 11 |
| 34.8 | 2.578 | 9 |

*impurity peak (c) The FeAPSO-20 compositions are generally characterized by the data of Table XII below:

TABLE XII

| 2θ | d, (Å) | Relative Intensity |
|---|---|---|
| 13.95–14.0 | 6.34–6.33 | m–vs |
| 19.8–20.0 | 4.48–4.44 | m |
| 24.3–24.5 | 3.663–3.633 | m–vs |
| 28.15–28.4 | 3.169–3.143 | w |
| 31.6–31.7 | 2.831–2.823 | w |
| 34.7–34.8 | 2.585–2.578 | w |

(d) The FeAPSO-20 compositions for which x-ray powder diffraction data have been obtained have patterns which are characterized by the x-ray powder diffraction pattern shown in Table XIII, below:

TABLE XIII

| 2θ | d, (Å) | 100 × I/Io |
|---|---|---|
| 13.95–14.0 | 6.34–6.33 | 57–100 |
| 19.8–20.0 | 4.48–4.44 | 28–47 |
| 22.25–22.6 | 3.998–3.935 | 3–6 |
| 24.3–24.5 | 3.663–3.633 | 45–100 |
| 28.15–28.4 | 3.169–3.143 | 11–16 |
| 31.6–31.7 | 2.831–2.823 | 11–12 |
| 34.7–34.8 | 2.585–2.578 | 9–16 |
| 37.6 | 2.392 | 2–3 |
| 40.2–40.3 | 2.242–2.240 | 4 |
| 42.7–42.85 | 2.114–2.110 | 5 |
| 47.5–47.6 | 1.914–1.909 | 3–4 |
| 52.0 | 1.759 | 8 |

EXAMPLE 51

(a) FeAPSO-31, as prepared in example 34, was subjected to x-ray analysis. FeAPSO-31 was determined to have a characteristic x-ray powder diffraction pattern which contains the d-spacings set forth below:

| 2θ | d, (Å) | 100 × I/Io |
|---|---|---|
| 8.5 | 10.41 | 64 |
| 9.45* | 9.35 | 5 |
| 13.0 | 6.81 | 1 |
| 14.6 | 6.07 | 1 |
| 15.7 | 5.64 | 3 |
| 17.05 | 5.20 | 6 |
| 18.3 | 4.85 | 3 |
| 20.25 | 4.39 | 49 |
| 21.05* | 4.22 | 9 |
| 21.95 | 4.05 | 32 |
| 22.6 | 3.936 | 100 |
| 23.2 | 3.833 | 6 |
| 25.1 | 3.546 | 4 |
| 25.65 | 3.474 | 4 |
| 26.45 | 3.372 | 2 |
| 27.9 | 3.195 | 13 |
| 28.7 | 3.110 | 1 |
| 29.7 | 3.008 | 7 |
| 31.7 | 2.821 | 20 |
| 32.7 | 2.739 | 1 |
| 35.15 | 2.555 | 9 |
| 36.1 | 2.489 | 2 |
| 37.2 | 2.418 | 2 |
| 37.65 | 2.390 | 2 |
| 38.15 | 2.358 | 3 |
| 39.3 | 2.293 | 4 |
| 39.6 | 2.275 | 3 |
| 40.2 | 2.244 | 2 |
| 45.2 | 2.006 | 2 |
| 46.65 | 1.947 | 3 |
| 48.65 | 1.871 | 2 |
| 50.75 | 1.799 | 2 |
| 51.65 | 1.770 | 4 |
| 55.5 | 1.650 | 2 |

*Peak may contain impurity (b) A portion of the as-synthesized FeAPSO-31 of part (a) was calcined in air at 600° C. for about 2 hours. The calcined product was characterized by the x-ray powder diffraction pattern below:

| 2θ | d, (Å) | 100 × I/Io |
|---|---|---|
| 8.6 | 10.26 | 73 |
| 9.8* | 9.04 | 3 |
| 12.95 | 6.83 | 1 |
| 14.9 | 5.95 | 5 |
| 16.2 | 5.46 | 4 |
| 17.2 | 5.16 | 11 |
| 18.45 | 4.80 | 4 |
| 20.4 | 4.35 | 50 |
| 22.15 | 4.016 | 44 |
| 22.75 | 3.909 | 100 |
| 23.45 | 3.795 | 3 |
| 25.3 | 3.521 | 5 |
| 25.8 | 3.449 | 9 |
| 28.1 | 3.174 | 13 |
| 29.9 | 2.990 | 12 |
| 31.1** | 2.876 | 2 |
| 31.9 | 2.806 | 30 |
| 32.7 | 2.739 | 2 |
| 35.3 | 2.542 | 10 |
| 36.3 | 2.475 | 5 |
| 37.35 | 2.407 | 3 |
| 37.85 | 2.378 | 2 |
| 38.35 | 2.346 | 3 |
| 39.5 | 2.282 | 4 |
| 40.35 | 2.234 | 3 |
| 44.15 | 2.052 | 2 |
| 45.05* | 2.013 | 2 |
| 45.4 | 1.997 | 2 |
| 46.85 | 1.940 | 5 |
| 47.65 | 1.909 | 2 |
| 48.9 | 1.863 | 3 |
| 49.3 | 1.848 | 2 |
| 50.95 | 1.793 | 2 |
| 51.8 | 1.765 | 6 |
| 55.6 | 1.653 | 3 |

*Peak may contain impurity
**impurity peak (c) The FeAPSO-31 compositions are generally characterized by the data of Table XIV below:

TABLE XIV

| 2θ | d, (Å) | Relative Intensity |
|---|---|---|
| 8.5–8.6 | 10.40–10.28 | w–s |
| 20.2–20.4 | 4.40–4.35 | m |
| 21.1–21.2 | 4.21–4.19 | w |
| 22.0–22.1 | 4.040–4.022 | m |
| 22.6–22.7 | 3.934–3.917 | vs |
| 31.7–31.9 | 2.822–2.805 | w–m |

(d) The FeAPSO-31 compositions for which x-ray powder diffraction data have been obtained have patterns which are characterized by the x-ray powder diffraction pattern shown in Table XV below:

TABLE XV

| 2θ | d, (Å) | 100 × I/Io |
|---|---|---|
| 8.5-8.6 | 10.40-10.28 | 10-88 |
| 9.5-9.8 | 9.35-9.04 | 3-11 |
| 9.9 | 8.92 | 0-3 |
| 13.0-13.3 | 6.81-6.67 | 1-4 |
| 14.6-14.9 | 6.07-5.95 | 0-5 |
| 15.7-16.2 | 5.64-5.46 | 3-7 |
| 17.0-17.2 | 5.20-5.17 | 5-11 |
| 18.3-18.5 | 4.84-4.80 | 2-4 |
| 20.2-20.4 | 4.40-4.35 | 36-50 |
| 21.1-21.2 | 4.21-4.19 | 9-18 |
| 22.0-22.1 | 4.040-4.022 | 26-44 |
| 22.6-22.7 | 3.934-3.919 | 100 |
| 23.2-23.4 | 3.833-3.795 | 3-12 |
| 25.1-25.3 | 3.546-3.521 | 4-5 |
| 25.6-25.8 | 3.474-3.449 | 3-9 |
| 26.4-26.6 | 3.372-3.352 | 0-5 |
| 27.4-27.5 | 3.258-3.248 | 2-4 |
| 27.9-28.1 | 3.195-3.174 | 12-14 |
| 28.3 | 3.152 | 0-3 |
| 28.7-28.8 | 3.111-3.103 | 0-3 |
| 29.7-29.9 | 3.008-2.990 | 6-12 |
| 31.1 | 2.876 | 0-2 |
| 31.7-31.9 | 2.822-2.805 | 19-30 |
| 32.7-33.0 | 2.739-2.718 | 0-3 |
| 35.1-35.3 | 2.555-2.542 | 9-10 |
| 36.1-36.3 | 2.489-2.475 | 2-5 |
| 37.3-37.4 | 2.418-2.407 | 0-3 |
| 37.6-37.8 | 2.390-2.378 | 2-3 |
| 38.1-38.4 | 2.365-2.346 | 2-3 |
| 39.3-39.5 | 2.293-2.282 | 3-4 |
| 39.6-39.7 | 2.275-2.271 | 0-3 |
| 40.2-40.3 | 2.244-2.239 | 0-3 |
| 44.1 | 2.052 | 0-2 |
| 44.9 | 2.020 | 0-2 |
| 45.0-45.1 | 2.015-2.012 | 0-2 |
| 45.2-45.4 | 2.006-1.997 | 2-3 |
| 46.6-46.8 | 1.947-1.940 | 3-5 |
| 47.5-47.6 | 1.914-1.909 | 0-2 |
| 48.6-48.9 | 1.872-1.863 | 2-3 |
| 49.1-49.3 | 1.854-1.848 | 0-3 |
| 50.8-50.9 | 1.799-1.793 | 0-2 |
| 51.6-51.8 | 1.771-1.765 | 0-4 |
| 55.5-55.6 | 1.657-1.653 | 0-3 |

EXAMPLE 52

(a) FeAPSO-34, as prepared in example 3, was subjected to x-ray analysis. FeAPSO-34 was determined to have a characteristic x-ray powder diffraction pattern which contains the d-spacings set forth below:

| 2θ | d, (Å) | 100 × I/Io |
|---|---|---|
| 7.3* | 12.1 | 5 |
| 9.35 | 9.5 | 100 |
| 12.7 | 7.0 | 10 |
| 14.0 | 6.3 | 8 |
| 14.8* | 5.99 | 2 |
| 15.9 | 5.57 | 32 |
| 17.9 | 4.96 | 7 |
| 19.6* | 4.53 | 3(sh) |
| 20.4 | 4.35 | 50 |
| 22.3 | 3.99 | 6 |
| 22.9 | 3.88 | 2 |
| 25.1 | 3.548 | 10 |
| 25.7 | 3.466 | 11 |
| 27.5 | 3.243 | 2 |
| 28.2 | 3.164 | 2 |
| 29.4 | 3.038 | 2(sh) |
| 30.4 | 2.940 | 19 |
| 31.1 | 2.876 | 12 |
| 34.4 | 2.607 | 4 |
| 36.2 | 2.481 | 2 |
| 39.5 | 2.281 | 2 |
| 43.3 | 2.090 | 3 |
| 47.5 | 1.914 | 2 |
| 48.9 | 1.863 | 3 |
| 51.0 | 1.791 | 2 |

-continued

| 2θ | d, (Å) | 100 × I/Io |
|---|---|---|
| 53.0 | 1.728 | 2 |
| 54.5 | 1.684 | 1 |

*Impurity peak (b) A portion of the as-synthesized FeAPSO-34 of part (a) was calcined in air at 600° C. for about 2 hours. The calcined product was characterized by the x-ray powder diffraction pattern below:

| 2θ | d, (Å) | 100 × I/Io |
|---|---|---|
| 7.5* | 11.79 | 7 |
| 9.6 | 9.21 | 100 |
| 13.0 | 6.81 | 17 |
| 16.2 | 5.47 | 9 |
| 16.9 | 5.25 | 1 |
| 18.0 | 4.93 | 5 |
| 19.3 | 4.60 | 5 |
| 19.9* | 4.46 | 2 |
| 20.9 | 4.25 | 17 |
| 22.55 | 3.943 | 7 |
| 23.4 | 3.802 | 2 |
| 24.2 | 3.678 | 2 |
| 25.1 | 3.548 | 5 |
| 26.2 | 3.401 | 7 |
| 27.2* | 3.278 | 1 |
| 28.2 | 3.164 | 2 |
| 29.2 | 3.058 | 2 |
| 31.0 | 2.885 | 16 |

*Impurity peak (c) The FeAPSO-34 compositions are generally characterized by the data of Table XVI below:

TABLE XVI

| 2θ | d, (Å) | Relative Intensity |
|---|---|---|
| 9.35-9.7 | 9.46-9.12 | vs |
| 12.7-13.0 | 6.97-6.81 | w-m |
| 15.9-16.2 | 5.57-5.47 | w-m |
| 20.4-20.9 | 4.35-4.25 | w-s |
| 22.3-22.5 | 3.99-3.95 | vw-s |
| 25.7-26.2 | 3.466-3.401 | vw-m |

(d) The FeAPSO-34 compositions for which x-ray powder diffraction data have been obtained have patterns which are characterized by the x-ray powder diffraction pattern shown in Table XVII below:

TABLE XVII

| 2θ | d, (Å) | 100 × I/Io |
|---|---|---|
| 9.35-9.7 | 9.46-9.12 | 100 |
| 12.7-13.0 | 6.97-6.81 | 10-25 |
| 13.9-14.1 | 6.37-6.28 | 2-11 |
| 15.9-16.2 | 5.57-5.47 | 9-47 |
| 17.6-18.0 | 5.04-4.93 | 5-16 |
| 18.9-19.3 | 4.70-4.60 | 0-5 |
| 20.4-20.9 | 4.35-4.25 | 17-89 |
| 22.3-22.5 | 3.99-3.95 | 4-88 |
| 22.9-23.4 | 3.88-3.80 | 2-8 |
| 24.8-25.3 | 3.59-3.52 | 5-18 |
| 25.7-26.2 | 3.466-3.401 | 7-32 |
| 27.5-27.6 | 3.243-3.232 | 0-5 |
| 28.0-28.4 | 3.187-3.143 | 1-3 |
| 29.4-29.6 | 3.038-3.018 | 0-4(sh) |
| 30.4-30.6 | 2.940-2.922 | 0-28 |
| 31.0-31.2 | 2.885-2.867 | 2(sh)-17 |
| 32.4 | 2.763 | 0-1 |
| 34.4-34.6 | 2.607-2.592 | 0-13 |
| 35.9-36.3 | 2.501-2.475 | 0-3 |
| 39.5-39.6 | 2.281-2.276 | 0-3 |
| 43.3-43.4 | 2.090-2.085 | 0-4 |
| 47.5-47.6 | 1.914-1.910 | 0-5 |
| 48.6-49.1 | 1.873-1.855 | 0-7 |
| 50.6-51.1 | 1.804-1.787 | 0-3 |

TABLE XVII-continued

| 2θ | d, (Å) | 100 × I/Io |
|---|---|---|
| 53.0-53.2 | 1.728-1.722 | 0-3 |
| 54.5-54.6 | 1.684-1.681 | 0-1 |

EXAMPLE 53

(a) FeAPSO-35, as prepared in example 27, was subjected to x-ray analysis. FeAPSO-35 was determined to have a characteristic x-ray powder diffraction pattern which contains the d-spacings set forth below:

| 2θ | d, (Å) | 100 × I/Io |
|---|---|---|
| 8.7 | 10.19 | 5 |
| 11.0 | 8.03 | sh |
| 11.4** | 7.77 | 51 |
| 13.5 | 6.57 | 9 |
| 16.0 | 5.55 | 3 |
| 17.4 | 5.09 | 28 |
| 17.9 | 4.95 | 5 |
| 18.65** | 4.76 | 50 |
| 21.0 | 4.22 | 15 |
| 21.9 | 4.06 | 100 |
| 22.9** | 3.885 | 9 |
| 23.45 | 3.793 | 8 |
| 25.1 | 3.548 | 3 |
| 26.5** | 3.365 | 25 |
| 27.15 | 3.285 | 7 |
| 28.6 | 3.118 | 16 |
| 28.9* | 3.091 | (sh) |
| 29.7** | 3.010 | 27 |
| 32.2 | 2.780 | (sh) |
| 32.5** | 2.754 | 13 |
| 34.6 | 2.591 | 7 |
| 37.8* | 2.381 | 10 |
| 44.1** | 2.053 | 3 |
| 48.25* | 1.886 | 8 |
| 51.6 | 1.774 | 1 |
| 52.15** | 1.754 | 2 |
| 54.5** | 1.684 | 3 |

*peak may contain impurity
**impurity peak (b) The FeAPSO-35 compositions are generally characterized by the data of Table XVIII below:

TABLE XVIII

| 2θ | d, (Å) | Relative Intensity |
|---|---|---|
| 10.9-11.1 | 8.12-7.97 | vw-m |
| 13.2-13.5 | 6.71-6.56 | vw-w |
| 17.2-17.4 | 5.16-5.10 | w-m |
| 21.85-22.0 | 4.07-4.04 | vs |
| 23.2-23.8 | 3.834-3.739 | vw-m |
| 32.0-32.25 | 2.797-2.776 | vw-m |

(c) The FeAPSO-35 compositions are generally characterized by the x-ray powder diffraction pattern shown in Table XIX, below:

TABLE XIX

| 2θ | d, (Å) | 100 × I/Io |
|---|---|---|
| 8.6-8.7 | 10.28-10.19 | 0-14 |
| 10.9-11.1 | 8.12-7.97 | sh-38 |
| 13.2-13.5 | 6.71-6.56 | 7-19 |
| 15.8-16.2 | 5.61-5.47 | 1-6 |
| 17.2-17.4 | 5.16-5.10 | 11-41 |
| 17.75-17.9 | 5.00-4.95 | sh-8 |
| 20.8-21.25 | 4.27-4.18 | sh-15 |
| 21.85-22.0 | 4.07-4.040 | 100 |
| 23.2-23.8 | 3.834-3.739 | 0-20 |
| 24.9-25.1 | 3.576-3.548 | 0-3 |
| 26.9-27.15 | 3.314-3.285 | 0-15 |
| 28.5-28.65 | 3.132-3.114 | sh-16 |
| 28.8-29.0 | 3.100-3.082 | 0-sh |
| 32.0-32.25 | 2.797-2.776 | sh-24 |

TABLE XIX-continued

| 2θ | d, (Å) | 100 × I/Io |
|---|---|---|
| 34.5-34.9 | 2.600-2.571 | 3-8 |
| 37.7-38.1 | 2.386-2.362 | 6-10 |

EXAMPLE 54

(a) FeAPSO-44, as prepared in example 32, was subjected to x-ray analysis. FeAPSO-44 was determined to have a characteristic x-ray powder diffraction pattern which contains at least the d-spacings set forth below:

| 2θ | d, (Å) | 100 × I/Io |
|---|---|---|
| 7.5** | 11.80 | 670 |
| 9.5 | 9.29 | 94 |
| 12.95* | 6.83 | 70 |
| 14.95** | 5.92 | 132 |
| 16.15 | 5.48 | 30 |
| 17.4 | 5.10 | 7 |
| 19.0 | 4.67 | 7 |
| 19.8** | 4.48 | 326 |
| 21.0* | 4.23 | 332 |
| 21.8 | 4.07 | 34 |
| 22.45** | 3.963 | 631 |
| 23.1 | 3.850 | 7 |
| 24.5 | 3.635 | 100 |
| 24.7** | 3.604 | 40 |
| 26.0* | 3.425 | 193 |
| 27.15** | 3.283 | 30 |
| 28.05* | 3.180 | 19 |
| 29.05** | 3.075 | 110 |
| 30.1* | 2.966 | 137 |
| 30.9 | 2.894 | 40 |
| 33.0 | 2.714 | 7 |
| 33.65** | 2.664 | 37 |
| 34.6** | 2.591 | 105 |
| 35.55 | 2.525 | 128 |
| 37.0** | 2.430 | 28 |
| 37.65** | 2.389 | 82 |
| 42.3* | 2.137 | 23 |
| 42.55* | 2.125 | 17 |
| 43.7* | 2.072 | 15 |
| 45.1** | 2.011 | 14 |
| 47.75* | 1.904 | 36 |
| 51.6** | 1.77 | 17 |
| 52.0** | 1.758 | 16 |
| 55.8** | 1.647 | 19 |

*Peak might contain impurity
**impurity peak (b) The FeAPSO-44 compositions are generally characterized by the data of Table XX below:

TABLE XX

| 2θ | d, (Å) | Relative Intensity* |
|---|---|---|
| 9.5 | 9.31 | m |
| 12.95 | 6.83 | m |
| 16.15 | 5.49 | vw |
| 21.0 | 4.23 | vs |
| 24.5 | 3.631 | m |
| 30.9 | 2.894 | w |

*peak intensities were low and may affect accuracy (c) The FeAPSO-44 compositions for which x-ray powder diffraction data have been obtained have patterns which are characterized by the x-ray powder diffraction pattern shown in Table XXI below:

TABLE XXI

| 2θ | d, (Å) | 100 × I/Io* |
|---|---|---|
| 9.5 | 9.31 | 28 |
| 12.95 | 6.83 | 21 |
| 16.15 | 5.49 | 9 |
| 17.4 | 5.10 | 2 |
| 19.0 | 4.67 | 2 |

TABLE XXI-continued

| 2θ | d, (Å) | 100 × I/Io* |
|---|---|---|
| 21.0 | 4.23 | 100 |
| 21.8 | 4.07 | 10 |
| 23.1 | 3.850 | 2 |
| 24.5 | 3.635 | 30 |
| 26.0 | 3.427 | 58 |
| 28.05 | 3.180 | 6 |
| 30.1 | 2.966 | 11 |
| 30.9 | 2.894 | 12 |
| 33.0 | 2.714 | 2 |
| 35.55 | 2.525 | 39 |
| 42.3 | 2.137 | 7 |
| 42.55 | 2.125 | 5 |
| 43.7 | 2.072 | 5 |
| 47.75 | 1.904 | 11 |

*peak intensities were low and may effect accuracy

EXAMPLE 55

(a) FeAPSO-46, as prepared in example 38 was subjected to x-ray analysis. FeAPSO-46 was determined to have a characteristic x-ray powder diffraction pattern which contains the d-spacings set forth below:

| 2θ | d, (Å) | 100 × I/Io |
|---|---|---|
| 6.6 | 13.42 | 3 |
| 7.75 | 11.38 | 100 |
| 12.45 | 7.11 | 2 |
| 13.2 | 6.70 | 2 |
| 13.8 | 6.41 | 1 |
| 15.0 | 5.91 | 1 |
| 15.35 | 5.77 | 1 |
| 16.7 | 5.31 | 2 |
| 17.3 | 5.13 | <1 |
| 19.9 | 4.47 | 1 |
| 20.6 | 4.31 | 3 |
| 21.65 | 4.11 | 7 |
| 22.9 | 3.885 | 4 |
| 24.3 | 3.660 | 3 |
| 25.2 | 3.534 | <1 |
| 26.95 | 3.307 | 3 |
| 27.85 | 3.206 | 2 |
| 28.35 | 3.147 | 1 |
| 28.85 | 3.093 | 3 |
| 29.95 | 2.985 | 1 |
| 30.2 | 2.959 | <1 |
| 30.95 | 2.889 | <1 |
| 31.35 | 2.855 | 2 |
| 31.8 | 2.814 | <1 |
| 33.05 | 2.711 | 1 |
| 34.4 | 2.606 | 1 |
| 36.05 | 2.490 | 3 |
| 36.7 | 2.448 | <1 |
| 39.9 | 2.259 | <1 |
| 41.25 | 2.188 | <1 |
| 44.2 | 2.049 | 1 |
| 47.85 | 1.902 | 1 |
| 50.4 | 1.811 | <1 |
| 51.7 | 1.768 | <1 |
| 52.5 | 1.743 | <1 |

(b) A portion of the as-synthesized FeAPSO-46 of part (a) was calcined in air at 500° C. for about 2 hours. The calcined product was characterized by the x-ray powder diffraction pattern below:

| 2θ | d, (Å) | 100 × I/Io |
|---|---|---|
| 6.85 | 12.92 | 9 |
| 8.0 | 11.04 | 100 |
| 13.6 | 6.51 | 4 |
| 15.35 | 5.76 | 3 |
| 16.0 | 5.55 | 3 |
| 17.15 | 5.17 | 3 |
| 21.3 | 4.17 | 2 |
| 22.2 | 4.006 | 2 |
| 23.45 | 3.793 | 2 |
| 24.9 | 3.575 | 2 |
| 27.6 | 3.232 | 2 |
| 32.0 | 2.797 | 2 |

(c) The FeAPSO-46 compositions are generally characterized by the data of Table XXII below.

TABLE XXII

| 2θ | d, (Å) | Relative Intensity |
|---|---|---|
| 6.6–6.8 | 13.39–13.00 | vw |
| 7.8–8.0 | 11.33–11.05 | vs |
| 13.2–13.6 | 6.71–6.51 | vw |
| 21.65–22.2 | 4.10–4.00 | vw |
| 22.9–23.45 | 3.883–3.793 | vw |
| 26.95–27.6 | 3.308–3.232 | vw |

(d) The FeAPSO-46 compositions for which x-ray powder diffraction data have been obtained to data have patterns which are characterized by the x-ray powder diffraction pattern shown in Table XXIII below:

TABLE XXIII

| 2θ | d, (Å) | 100 × I/Io |
|---|---|---|
| 6.6–6.8 | 13.39–13.00 | 3–9 |
| 7.8–8.0 | 11.33–11.05 | 100 |
| 12.45–12.6 | 7.11–7.03 | 0–3 |
| 13.2–13.6 | 6.71–6.51 | 2–4 |
| 13.8–14.0 | 6.41–6.33 | 1–2 |
| 15.0–15.35 | 5.91–5.76 | 1–3 |
| 15.35–16.0 | 5.77–5.55 | 1–3 |
| 16.7–17.15 | 5.31–5.17 | 2–3 |
| 17.3 | 5.13 | 0–1 |
| 19.9–20.5 | 4.47–4.43 | 1–2 |
| 20.6–21.3 | 4.31–4.17 | 2–3 |
| 21.65–22.2 | 4.10–4.00 | 2–8 |
| 22.9–23.45 | 3.883–3.793 | 2–4 |
| 24.3–24.9 | 3.659–3.575 | 2–3 |
| 25.2 | 3.534 | 0–1 |
| 26.95–27.6 | 3.308–3.232 | 2–4 |
| 27.85–27.95 | 3.206–3.190 | 0–3 |
| 28.35–28.55 | 3.147–3.125 | 0–2 |
| 28.85–29.05 | 3.093–3.076 | 0–3 |
| 29.95–30.1 | 2.985–2.968 | 0–1 |
| 30.2 | 2.959 | 0–1 |
| 30.95 | 2.889 | 0–1 |
| 31.3–32.0 | 2.855–2.797 | 2 |
| 31.8–32.05 | 2.814–2.792 | 0–1 |
| 33.05 | 2.711 | 0–1 |
| 34.4 | 2.608 | 0–1 |
| 36.05–36.2 | 2.490–2.481 | 0–3 |
| 36.7 | 2.448 | 0–1 |
| 39.9 | 2.259 | 0–1 |
| 41.25 | 2.188 | 0–1 |
| 44.2–44.35 | 2.049–2.043 | 0–1 |
| 47.8–48.0 | 1.902–1.895 | 0–1 |
| 50.4 | 1.811 | 0–1 |
| 51.7 | 1.768 | 0–1 |
| 52.5 | 1.743 | 0–1 |

EXAMPLE 56

In order to demonstrate the catalytic activity of the FeAPSO compositions, calcined samples of FeAPSO products were tested for the catalytic cracking of n-butane using a bench-scale apparatus.

The reactor was a cylindrical quartz tube 254 mm. in length and 10.3 mm I.D. In each test the reactor was loaded with particles of the selected FeAPSO which were 20–40 mesh (U.S. std.) in size and in an amount of from 0.5 to 5 grams, the quantity being selected so that the conversion of n-butane was at least 5% and not more than 90% under the test conditions. The samples had been previously calcined in air or nitrogen to remove organic materials from the pore system, and were activated in situ in the reactor in a flowing stream of helium at 500° C. for one hour. The feedstock was a helium and n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of the FeAPSO compositions. The $k_A$ value (cm$^3$/g min) obtained for the FeAPSO compositions are set forth, below, in Table XXIV:

TABLE XXIV

| FeAPSO of Example No.:[1] | Rate Constant ($k_A$) |
|---|---|
| FeAPSO—5 (Ex. 12) | 0.5 |
| FeAPSO—11 (Ex. 10) | 0.7 |
| FeAPSO—31 (Ex. 34) | 1.3 |
| FeAPSO—46 (Ex. 37) | 0.9 |

[1]FeAPSO were calcined as follows prior to being activated:
(a) FeAPSO-5: at 600° C. in air for 2 hours;
(b) FeAPSO-11: at 600° C. in air for 2.25 hours;
(c) FeAPSO-31: at 500° C. to 600° C. in air for 2 hours; and,
(d) FeAPSO-46: heated from 100° C. to 600° C. in nitrogen over a 2-hour period.

PROCESS APPLICATIONS

The FeAPSO compositions of the present invention are, in general, hydrophilic and adsorb water preferentially over common hydrocarbon molecules such as paraffins, olefins and aromatic species, e.g., benzene, xylenes and cumene. Thus, the FeAPSOs as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These FeAPSOs are therefore suitably employed in the drying of reformer hydrogen streams and in the drying of oxygen, nitrogen or air prior to liquifaction.

The present FeAPSO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalyst compositions having silica or alumina bases. Of the general class, those species having pores larger than about 4 Å are preferred for catalytic applications.

Among the hydrocarbon conversion reactions catalyzed by FeAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using FeAPSO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The FeAPSO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such a normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (hydrogen to hydrocarbon) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$-$C_{20}$. Contact time between the feedstock and the catalyst is generally relatively short to avoid undesireable side reactions such as olefin polymerization and paraffin cracking. LHSV values in the range of 0.1 to 10, preferably 1.0 to 6.0 are suitable.

The unique crystal structure of the present FeAPSO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with FeAPSO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the FeAPSO catalyst in conjunction with a Group VIII non-noble metal cation such as zinc and nickel.

In catalytic dealkylation wherein it is desired to cleave paraffinic side chains from aromatic nuclei without substantially hydrogenating the ring structure, relatively high temperatures in the range of about 800°-1000° F. are employed at moderate hydrogen pressures of about 300-1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed that are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°-900° F., while paraffins, naphthenes and alkyl aromatics are isomerized at temperatures of 700°-1000° F. Particularly desirable isomerization reactions contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexene to isohexene, cyclohexene to methylcyclopentene etc. The preferred form of the catalyst is a combination of the FeAPSO with polyvalent metal compounds (such as sulfides) of metals of Group II-A, Group II-B and rare earth metals. For alkylation and dealkylation processes the FeAPSO compositions having pores of at least 5 Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In the alkylation of benzene, toluene and xylene, the preferred alkylating agents are olefins such as ethylene and propylene.

We claim:

1. Crystalline molecular sieves having framework structures of $FeO_2$, $AlO_2$, $PO_2$ and $SiO_2$ tetrahedral units and having a unit empirical formula:

$$mR:(Fe_wAl_xP_ySi_z)O_2$$

wherein "R" represents at least one organic templating agent present, in the intracrystalline pore system; "m" represents the molar amount of "R" present per mole of $(Fe_wAl_xP_ySi_z)O_2$ and has a value of zero to about 0.3; and "w", "x", "y" and "z" represent the mole fractions of iron, aluminum, phosphorus and silicon, respectively, present as tetrahedral oxides, each having a value of at least 0.01, said mole fractions being such that they are within the pentagonal compositional area defined by points A, B, C, D and E of FIG. 1.

2. Crystalline molecular sieves according to claim 1 wherein the mole fractions of iron, aluminum, phosphorus and silicon are within the tetragonal compositional area defined by points a, b, c and d of FIG. 2.

3. The crystalline molecular sieves of claims 1 or 2 having a characteristic x-ray powder diffraction pattern which contains at least the d-spacings set forth in Table A.

4. The crystalline molecular sieves of claims 1 or 2 having a characteristic x-ray powder diffraction pattern which contains at least the d-spacings set forth in Table B.

5. The crystalline molecular sieves of claims 1 or 2 having a characteristic x-ray powder diffraction pattern which contains at least the d-spacings set forth in Table C.

6. The crystalline molecular sieves of claims 1 or 2 having a characteristic x-ray powder diffraction pattern which contains at least the d-spacings set forth in Table D.

7. The crystalline molecular sieves of claims 1 or 2 having a characteristic x-ray powder diffraction pattern which contains at least the d-spacings set forth in Table E.

8. The crystalline molecular sieves of claims 1 or 2 having a characteristic x-ray powder diffraction pattern which contains at least the d-spacings set forth in Table F.

9. The crystalline molecular sieves of claims 1 or 2 having a characteristic x-ray powder diffraction pattern which contains at least the d-spacings set forth in Table G.

10. The crystalline molecular sieves of claims 1 or 2 having a characteristic x-ray powder diffraction pattern which contains at least the d-spacings set forth in Table H.

11. The crystalline molecular sieves of claims 1 or 2 having a characteristic x-ray powder diffractions pattern which contains at least the d-spacing set forth in Table J.

12. The crystalline molecular sieves of claims 1 or 2 having a characteristic x-ray powder diffraction pattern which contains at least the d-spacings set forth in Table K.

13. Process for preparing the crystalline molecular sieves of claim 1 having three dimensional microporous framework structures which comprises providing a reaction mixture at an effective temperature and for an effective time sufficient to produce the molecular sieves of claim 1, said reaction mixture being expressed in terms of molar oxide ratios of:

$$eR:(Fe_wAl_xP_ySi_z)O_2:fH_2O$$

wherein "R" is an organic templating agent; "e" is the molar amount of "R" and is an effective amount greater than zero to about 6; "f" has a value of from zero to about 500; and "w", "x", "y" and "z" represent the mole fractions, respectively, of iron, aluminum, phosphorus and silicon in the $(Fe_wAl_xP_ySi_z)O_2$ constituent, and each has a value of at least 0.01.

14. The process of claim 13 wherein the values of "w", "x", "y" and "z" are within the pentagonal area defined by points F, G, H, I and J of FIG. 3.

15. Process according to claim 13 wherein the reactive source of phosphorus in the reaction mixture is orthophosphoric acid.

16. Process according to claim 13 wherein the reactive source of iron is selected from the group consisting of iron (II) acetate, iron (II) sulfate, and mixtures thereof.

17. Process according to claim 13 wherein the reactive source of silicon is silica.

18. Process according to claim 13 wherein the reactive source of aluminum in the reaction mixture is at least one compound selected from the group consisting of pseudo-boehmite and aluminum alkoxide, and the source of phosphorus is orthophosphoric acid.

19. Process according to claim 18 wherein the aluminum alkoxide is aluminum isopropoxide.

20. Process according to claims 13 where the organic templating agent is selected from the group consisting of quaternary ammonium or quaternary phosphonium compounds of the formula:

$$R_4X^+$$

wherein X is nitrogen or phosphorous and each R is alkyl containing between 1 and about 8 carbon atoms or aryl.

21. Process according to claim 13 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; dicyclohexylamine; N,N-dimethylethanolamine; chlorine; N,N-dimethylpiperazine; 1,4-diazabicyclo-(2,2,2)octane; N-methylpiperidine; 3-methylpiperidine; N-methylcyclohexylamine; 3-methylpyridine; 4-methylpyridine; quinuclidine; N,N-dimethyl-1,4-diazabicyclo(2,2,2)octane ion; tetramethylammonium ion; tetrabutylammonium ion, tetrapentylammonium ion; di-n-butylamine; neopentylamine; di-n-pentylamine; isopropylamine; t-butylamine; ethylenediamine pyrrolidine; 2-imidazolidone; di-n-propylamine; and a polymeric quaternary ammonium salt $[(C_{14}H_{32}N_2)(oH)]_x$ wherein x is a value of at least 2.

22. Process of claim 13 wherein the organic templating agent is an amine.

23. Crystalline molecular sieve prepared by calcining the composition of claim 1 or claim 2 at a temperature sufficiently high to remove at least some of the organic templating agent present in the intracrystalline pore system.

24. The crystalline molecular sieves of claims 1 or 2 wherein the values of "w" and "z" have the following mole fraction values: "w" is $\geq 0.04$; and "z" is $\geq 0.02$.

25. The process of claim 13 wherein "f" has a value of from about 2 to about 500.

26. The process of claim 25 wherein "f" has a value of from about 2 to about 300.

* * * * *